United States Patent
Toth et al.

(10) Patent No.: US 10,485,484 B2
(45) Date of Patent: *Nov. 26, 2019

(54) ELONGATED CONDUCTORS AND METHODS OF MAKING AND USING THE SAME

(71) Applicant: Autonomix Medical, Inc., Ivyland, PA (US)

(72) Inventors: Landy Toth, Ivyland, PA (US); Robert Schwartz, Ivyland, PA (US)

(73) Assignee: Autonomix Medical, Inc., Ivyland, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/274,527

(22) Filed: Feb. 13, 2019

(65) Prior Publication Data

US 2019/0175112 A1    Jun. 13, 2019

Related U.S. Application Data

(63) Continuation of application No. 16/119,979, filed on Aug. 31, 2018, now Pat. No. 10,238,340, which is a
(Continued)

(51) Int. Cl.
*A61B 5/00* (2006.01)
*A61N 1/05* (2006.01)
(Continued)

(52) U.S. Cl.
CPC .......... *A61B 5/6876* (2013.01); *A61B 5/6852* (2013.01); *A61B 18/1492* (2013.01);
(Continued)

(58) Field of Classification Search
CPC ........ H01B 7/02; H01B 7/009; H01B 7/0846; H01B 7/08; H01B 7/0823; A61B 5/6876; A61B 5/6852; A61M 25/00
See application file for complete search history.

(56) References Cited

U.S. PATENT DOCUMENTS 4,635,359 A   1/1987  Nozick
5,902,962 A   5/1999  Gazdzinski
(Continued)

FOREIGN PATENT DOCUMENTS

EP    2789366 A1   10/2014
JP    S6048621 U    4/1985
(Continued)

*Primary Examiner* — Timothy J Thompson
*Assistant Examiner* — Amol H Patel
(74) *Attorney, Agent, or Firm* — Bret E. Field; Bozicevic, Field & Francis LLP

(57) ABSTRACT

Elongated conductors are provided. Aspects of the elongated conductors include: an elongated structure having a proximal region and a distal region, where the elongated conductor includes two or more insulated conducting members that are in fixed relative position along at least a portion of the elongated structure and extend from the proximal region to the distal region. A pattern of insulation openings among the insulated conducting members is present at one or both of the proximal and distal regions. Aspects of the invention further include methods of making the elongated conductors, as well as devices that include the elongated conductors.

20 Claims, 8 Drawing Sheets

Related U.S. Application Data continuation of application No. 15/646,972, filed on Jul. 11, 2017, now Pat. No. 10,092,241, which is a continuation of application No. 15/159,615, filed on May 19, 2016, now Pat. No. 9,730,639.

(60) Provisional application No. 62/169,347, filed on Jun. 1, 2015.

(51) Int. Cl.

| | | |
|---|---|---|
| *A61B 18/14* | (2006.01) | |
| *A61N 1/04* | (2006.01) | |
| *H01B 13/06* | (2006.01) | |
| *H01B 7/08* | (2006.01) | |
| *A61M 25/00* | (2006.01) | |
| *H01B 7/02* | (2006.01) | |
| *A61B 17/00* | (2006.01) | |
| *A61B 18/00* | (2006.01) | |

(52) U.S. Cl.
CPC ........... *A61M 25/00* (2013.01); *A61N 1/0488* (2013.01); *A61N 1/05* (2013.01); *H01B 7/02* (2013.01); *H01B 7/0846* (2013.01); *H01B 13/06* (2013.01); *A61B 2017/00526* (2013.01); *A61B 2018/00178* (2013.01); *A61B 2562/125* (2013.01); *A61B 2562/222* (2013.01); *H01B 7/0892* (2013.01)

(56) References Cited

U.S. PATENT DOCUMENTS

| | | | |
|---|---|---|---|
| 6,177,635 | B1* | 1/2001 | Sugiura ............... B60R 16/0215 174/138 G |
| 8,382,666 | B1 | 2/2013 | Mao et al. |
| 2002/0079129 | A1 | 6/2002 | Klesing et al. |
| 2005/0092517 | A1* | 5/2005 | Fan ........................ F21S 4/24 174/117 FF |
| 2006/0237218 | A1 | 10/2006 | Glew |
| 2011/0028816 | A1 | 2/2011 | Simpson et al. |
| 2012/0283570 | A1 | 11/2012 | Tegg |
| 2013/0111743 | A1 | 5/2013 | Ho |
| 2014/0090883 | A1* | 4/2014 | Gundel ............... H01B 7/0838 174/350 |
| 2016/0260521 | A1 | 9/2016 | Namiki et al. |

FOREIGN PATENT DOCUMENTS

| | | |
|---|---|---|
| JP | 2012-238509 A | 12/2012 |
| WO | WO2013112844 A2 | 8/2013 |

* cited by examiner

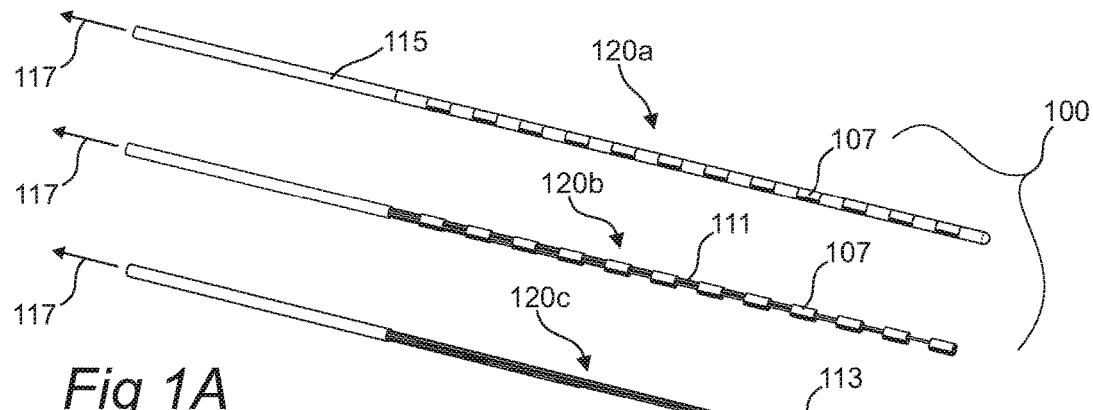
*Fig 1A*
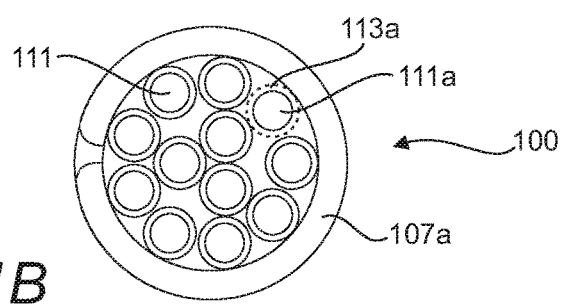
*Fig 1B*
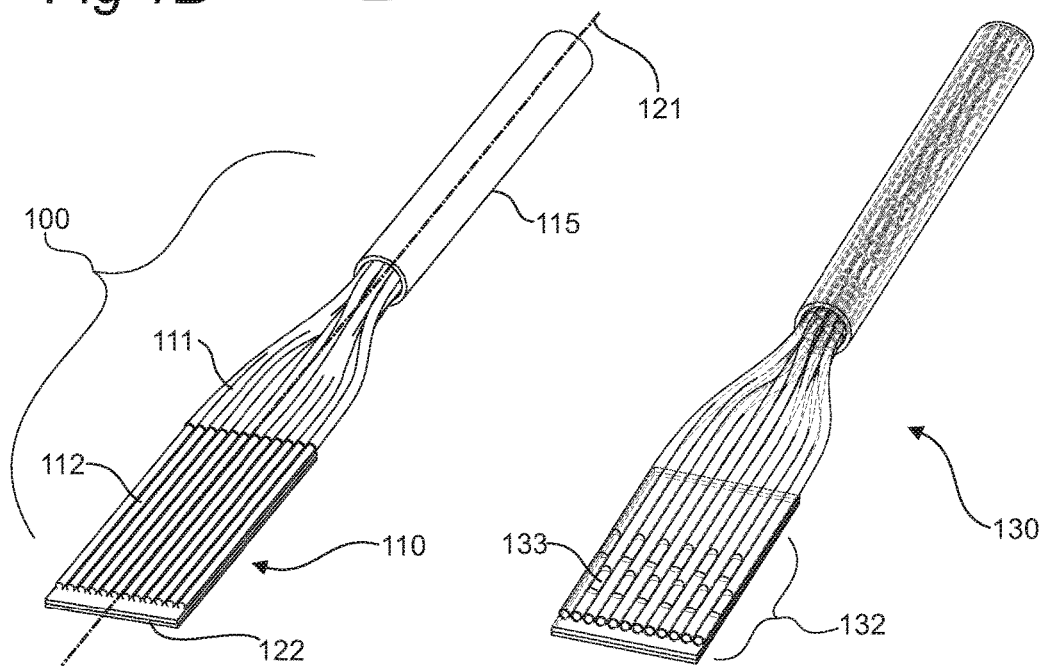
*Fig 1C*     *Fig 1D*

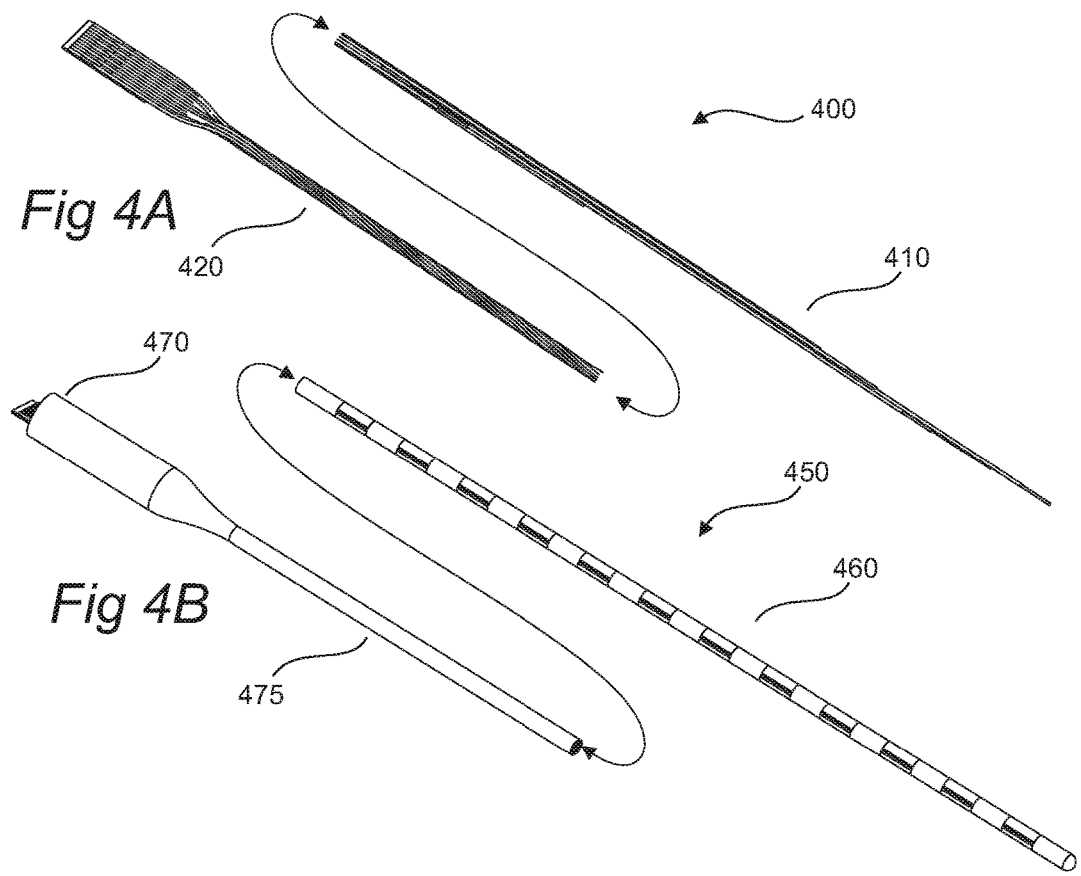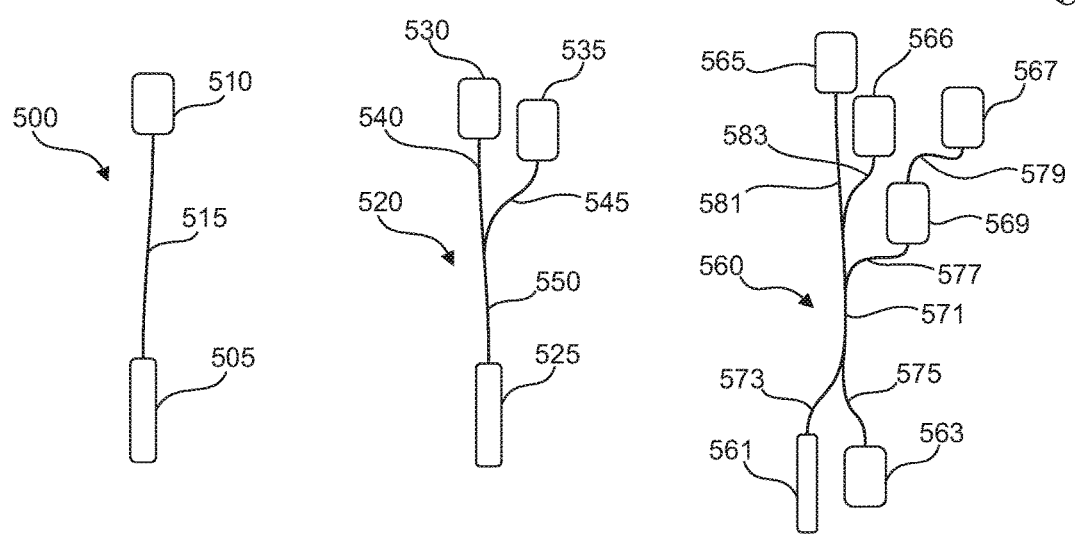

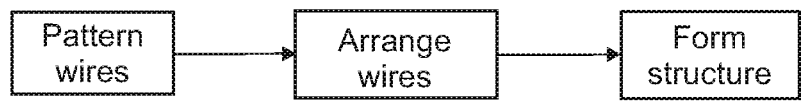
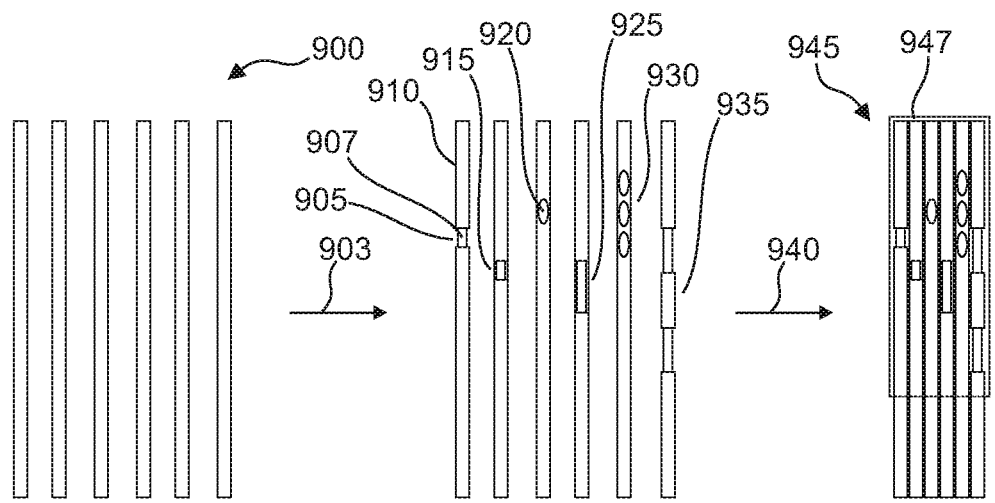
Fig 8A
Fig 9A
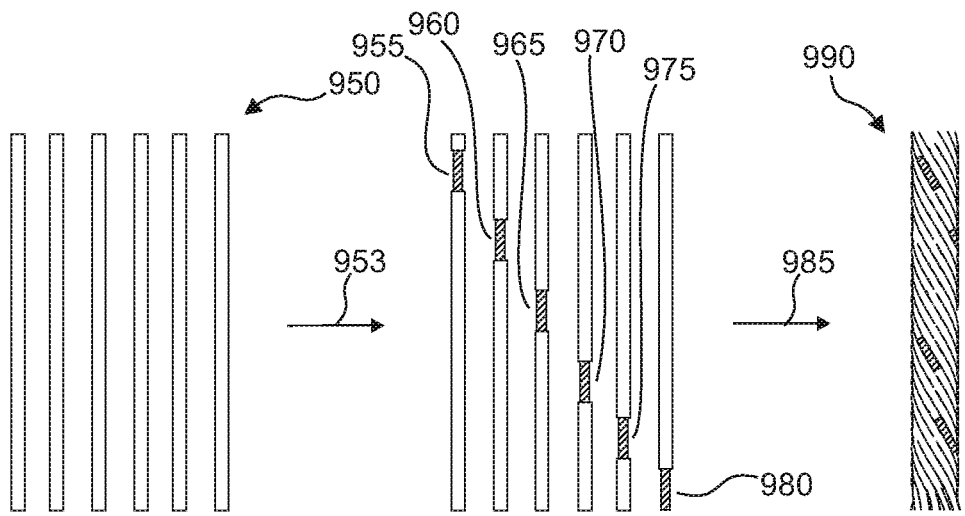
Fig 9B

ELONGATED CONDUCTORS AND METHODS OF MAKING AND USING THE SAME

CROSS-REFERENCE TO RELATED APPLICATIONS

Pursuant to 35 U.S.C. § 119 (e), this application claims priority to the filing date of the U.S. Provisional Patent Application Ser. No. 62/169,347, filed Jun. 1, 2015, the disclosure of which is incorporated herein by reference.

INTRODUCTION

Elongated conductors, such as elongated electrical conductors, find use in a variety of different devices used in many aspects of everyday life. For example, elongated electrical conductors find use a variety of medical devices, including interventional, minimally invasive, surgical and implantable devices. Medical devices currently in use include "smart" sensing and therapeutic guidewires, which may include a sensor (pressure, thermocouple, etc.) and therapeutic technology located at the tip of a guidewire. In such devices, 2 or 3 wires are generally necessary to interface with the sensor. The sensor is most often a simple bridge based sensor, or a variable resistance based sensor, etc.

Another type of medical device that includes an elongated conductor is a general electrophysiology catheter. General electrophysiology catheters often include a plurality of macro electrodes, usually in the form of ring electrodes, concentrically placed along a catheter tip. Macroscopic wires for each electrode are threaded through the catheter body back to an extracorporeal connector, and then to a connection box, and other signal conditioning electronics.

Elongated electrical conductors employed in today's medical devices, as well as other types of devices, generally have a very low wire count and a large external connector. During production of such devices, the distal and proximal connections are performed by hand or by machine, wire by wire. Wire sorting (to make the correct connections at each end), is achieved by color-coding and visual inspection, or by inline impedance measurement (which is still a wire by wire check and connect protocol). Also, after identification, the wires are generally wire-bonded to an electrode, chip, etc. of an effector at one end and then individually soldered into a connector at the other end. This manufacturing protocol is time consuming and expensive.

SUMMARY

Elongated conductors are provided. Aspects of the elongated conductors include: an elongated structure having a proximal region and a distal region, where the elongated conductor includes two or more insulated conducting members that are in fixed relative position along at least a portion of the elongated structure and extend from the proximal region to the distal region. A pattern of insulation openings among the insulated conducting members is present at one or both of the proximal and distal regions. Aspects of the invention further include methods of making the elongated conductors, as well as devices that include the elongated conductors.

BRIEF DESCRIPTION OF THE FIGURES

FIG. 1A provides a view of a proximal end of an elongated conductor having an axially aligned pattern of insulation openings, in accordance with an embodiment of the invention.

FIG. 1B provides a view of a cross section of the proximal end of the elongated conductor of FIG. 1A, in accordance with an embodiment of the invention.

FIGS. 1C-1E provide views of distal ends of elongated conductor assemblies having a transversely aligned pattern of insulation openings, in accordance with embodiments of the invention.

FIGS. 4A and 4B provide views of an elongate conductor and a final catheter body constructed from the elongate conductor, in accordance with an embodiment of the invention.

FIGS. 5A-5C provide schematics of elongate conductors demonstrating a range of end interconnection options, in accordance with embodiments of the invention.

FIG. 8A provides a schematic of portions of a method of fabricating an elongated conductor, in accordance with an embodiment of the invention.

FIGS. 9A-9B provide illustrations of steps of a method for fabricating an elongated conductor, in accordance with an embodiment of the invention.

DETAILED DESCRIPTION

Figure 1E:
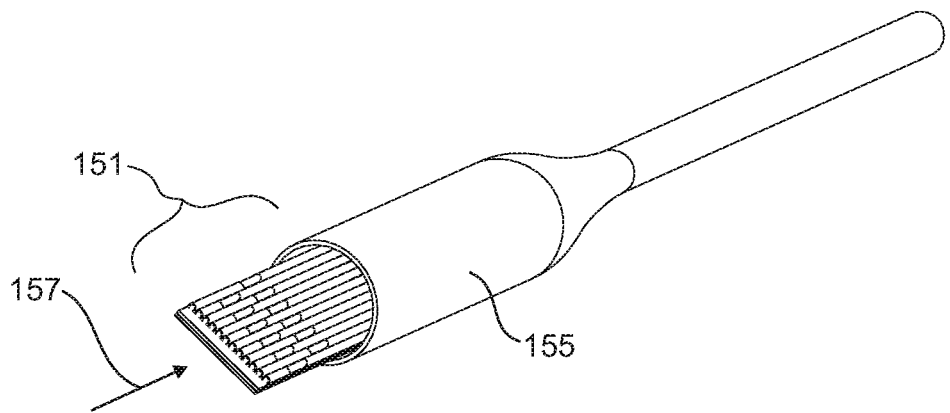

Elongated conductors are provided. Aspects of the elongated conductors include: an elongated structure having a proximal region and a distal region, where the elongated conductor includes two or more insulated conducting members that are in fixed relative position along at least a portion of the elongated structure and extend from the proximal region to the distal region. A pattern of insulation openings among the insulated conducting members is present at one or both of the proximal and distal regions. Aspects of the invention further include methods of making the elongated conductors, as well as devices that include the elongated conductors.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing various aspects of the invention, elongated conductors will be described first in greater detail, followed by a review of embodiments of methods of producing the conductors, as well as a review of various devices that may include the conductors.

Elongated Conductors

As summarized above, aspects of the invention include elongated conductors. The phrase "elongated conductor" as used herein refers to an elongated structure having a proximal region and a distal region, which structure is configured to convey some entity, e.g., electrical current, charge, light, heat, a fluid, a gel, a biological sample, etc., from the proximal region to the distal region or vice versa. As the elongated conductor is elongated, the elongated conductor has an elongated structure in which the length (extending from the proximal end of the proximal region to the distal end of the distal region) is longer than the longest cross-sectional dimension of the structure. While the ratio of length to longest cross-sectional dimension may vary, in some instances this ratio ranges from 20:1 to 50,000:1, such as 750:1 to 7,500:1, and including 1,000:1 to 5,000:1. In some instances, the elongated structure has a length ranging from 5 to 3,000 mm, such as 50 to 2,000 mm and including 750 to 1750 mm, and a longest cross-sectional dimension (e.g., diameter in those embodiments where the conductor is cylindrical in shape) ranging from 0.025 to 20.0 mm, such as 0.10 to 5.0 mm and including 0.10 to 1.0 mm. The cross-sectional shape of the conductor may vary, where examples of cross-sectional shapes that may be found in the conductors include, but are not limited to: rectilinear shapes, e.g., rectangular, square, triangular, trapezoidal, etc., curvilinear shapes, e.g., circular, oval, etc.; as well as irregular shapes. In some instances, the structure of the elongated conductor has a circular cross section, such that the structure is cylindrical.

In the broadest sense, the elongated conductors may be configured to convey different entities, e.g., electrical current, charge, light, heat, a fluid, a gel, a biological sample, etc. In some instances, the conductors are configured to convey electric current, such that they are electrical conductors. In some instances, the conductors are meant to convey light, such that they are optical fibers. In some instances, the elongated conductors may include a lumen, such that is meant to convey a fluid, a gel, a biological sample, etc.

Elongated conductors of the invention include two or more insulated conducting members that are in fixed relative position along at least a portion of the elongated structure and extend from the proximal region to the distal region of the elongated structure. As the conducting members are insulated and extend from a proximal region to a distal region of the elongated structure, they include an elongated component of a conductive material, e.g., an electrically conductive material, which is surrounded on all sides, e.g., coated, with an insulating material. The dimensions of the conductive material elongated component may vary, where in some instances the elongated component has a length ranging from 5 to 4,000 mm, such as 50 to 2,000 mm and a diameter ranging from 0.004 to 1.0 mm, such as 0.01 to 0.1 mm. The thickness of the insulating material, i.e., coating, may also vary, ranging in some instances from 0.0001 to 0.1 mm, such as 0.003 to 0.040 mm. Each of the insulated conducting members of the structure may have the same dimensions, or two or more the insulating conductive members may have different dimensions, e.g., differ from each other in terms of diameter such that at least two of the two or more insulated conductors comprise conductors of differing diameter, as desired.

The number of individual conducting members, e.g., electrically conducting wires, in the elongated structure may vary. In some instances, the number of conducting members ranges from 2 to 100,000, such as 2 to 500, e.g., 5 to 250, including 5 to 100, e.g., 5 to 75, 5 to 50 and 5 to 25. In some instances, the elongated conductors are characterized by having a high conducting member packing density. While the conducting member packing density may vary, in some instances the packing density ranges from 30% to 98%, such as 55% to 85% and including 60% to 78%. Embodiments of the elongated conductors are characterized by having high gauge conducting members with tight center-to-center conducting member pitch. In some instances, the gauge of the conductor may be 40 AWG or greater, such as 45 AWG or greater, including 50 AWG or greater, with a center to center conducting member pitch (i.e., an insulated conducting member pitch) ranging from 6 to 250 µm, such as 12 to 75 µm and including 15 to 30 µm.

The elongated conductors may include a plurality of conducting members with similar or different diameter. In some instances, an elongated conductor may include one or more conducting members with a first characteristic diameter (i.e. a characteristic maximal length in a transverse direction), and one or more conducting members with a second diameter. The ratio of the diameters between the first and the second conducting members may range from 1.1:1 to 20:1, such as 1.5:1 to 5:1 and including 1.5:1 to 2.5:1. The diameters of the conducting members may be sized based on the current carrying requirements of one or more components coupled thereto or a function provided thereto (e.g. such as for providing a power current, a signal, a low rate changing current, a high rate changing current, a waveguide function, etc.). In some instances, one or more of the second conducting members may be arranged and nested in and around one or more of the first conducting members. Such an arrangement may be advantageous to optimize or match the power requirements to the packing density of the overall elongated conductor.

The elongated conductors may include one or more sub-groupings of conducting members, each sub-grouping of conducting members arranged such that the spatial relationship between conducting members within the sub-group are relatively fixed with respect to each other. In some instances, one or more of the sub-group members may be pre-fixed so as to form a local shield around one or more members of the sub-group. In some instances, one or more pairs of sub-group members may be pre-fixed (e.g., linearly fixed together, wound together, etc.), so as to form a waveguide, a twisted pair, etc. Such an arrangement may be advantageous to control current flow and limit cross-talk between conducting members of the elongated conductor during use.

In some instances, two or more of the conducting members within an elongated conductor may be permanently bonded together at one or more lengths along the elongated conductor. Such permanent bonding may be advantageous to limit tribological noise associated with movement and flexure of the elongated conductor during use (e.g., such as during movement within lumen in a body, etc.).

In some instances, one or more of the conducting members may include a plurality of additional material layers, such as a first layer and a second layer. In instances, the first layer may be an insulating material, so as to substantially limit current flow, heat flow, light passage there through, as compared with passage along the length of the conducting material. In instances, the second layer may be a conducting layer, an insulating layer, a bonding layer, etc. In some instances, one or more conducting members in an elongated conductor may be bound together via the second layers of the conducting members. Thus, one or more portions of the elongated conductor may be a substantially monolithic body in terms of movement, etc. (i.e., in one or more regions of the elongated conductor, the conducting members may mechanically behave as a composite structure, frictional movement between conducting members being substantially minimal during flexure thereof). Such an instance may be advantageous for improving handle-ability of the elongated conductor during assembly, minimizing noise between conducting members during use, improve impedance tolerance between adjacent conducting members in the elongated conductor, etc.

In some instances, the second layer may be constructed, at least in part from a conducting material. The conducting material may substantially provide a return path for current through the conducting member, may complete a capacitive function of the conducting member (i.e., the capacitor formed from the inner conducting material, the first insulating layer, and the conducting layer), etc. In aspects, a plurality of such conducting members may be bonded together with the conducting layers, so as to provide an electrical shield for the elongated conductor, etc.

In some instances, the elongated conductor may include one or more additional structural members, the structural member providing mechanical rigidity, increased tensile strength, or the like for the overall elongated conductor. The structural member(s) may be arranged amid the conducting members, they may have a diameter that is similar to or different from the conducting members, or the like. In some instances, the structural members may be formed from ultra-high tensile strength fibers, the structural members arranged amid the conducting members to improve the overall strength of the elongated conductor. The dimensions of the structural members may be selected so as to provide enhanced packing density of the overall elongated conductor. In some instances, one or more conducting elements may include a binding material layer, the binding material layer providing a matrix for the structural members (i.e., a substantially continuous medium bridging the conducting members and/or the structural members). In some instances, the structural member(s) may be pre-treated (e.g., such as with a silane, siloxane, titanate, etc.) so as to bind to the binding material layer.

In some instances, an elongated conductor may include one or more wrapping sub-groups of conducting members and/or structural members, the wrapping sub-group configured so as to substantially surround one or more additional conducting members within the elongated conductor. Such a wrapping sub-group may be advantageous to form a shielding function, a return path, etc. along the length of the elongated conductor.

In some instances, an elongated conductor may include one or more regions along the length thereof, wherein a sub-group of conducting members provided therein, may be physically separated from each other. Such a configuration may be advantageous to separate sub-groups for attachment to separate connectors at the ends of or along an intermediate length of the elongated conductor.

As indicated above, the two or more insulated conducting members of the elongated conductor are in fixed relative position along at least a portion of the elongated structure.

By "fixed relative position" is meant that the conducting members are stably associated with each other, such that they do not move relative to each other, along at least portion of the elongated structure. As the two or more conducting members are stably associated along at least a portion, they do not move relative to each other in that portion under operating conditions for which the elongated conductors are configured to be used. In other words, the two or more insulated conducting members behave as a composite structure along at least a portion of the elongated structure. The two or more conducting members may be fixed relative to each other along substantially the entire elongated structure. Alternatively, there may be one or more regions along the length of the elongated structure where the two or more conducting members are not fixed relative to each other, e.g., to provide strain relief, along a sub-assembly, along a split region of the elongate conductor, etc. When present, the length of such region(s) (i.e., regions that are not stably associated with each other) may vary, ranging in some instances from 0.25 to 100 mm, such as 0.25 to 10 mm. The number of such regions may also vary, where in some instances the number ranges from 1 to 50, such as 1 to 10, e.g., 1 to 2.

Aspects of the elongated conductors include a pattern of insulation openings among the insulated conducting members at one or both of the proximal and distal regions, or even along intermediate regions along the length of the elongated conductor. By "pattern of insulation openings" is meant a collection of areas or windows (i.e., voids) among the insulation of the conductive members in the region of interest, e.g., proximal or distal region. The proximal and distal regions are located, respectively, in the vicinity of the proximal and distal ends of the conductive structure, where a given proximal and distal region will be positioned from 0 to 1,000 mm, such as 0 to 50 mm (e.g., 0 to 25 mm, 0 to 10 mm, including 0 to 5 mm) from its corresponding end of the structure. The area and shape of each insulation opening of the pattern may vary, where in some instances the area ranges from 10 $\mu m^2$ to 10 $mm^2$, such as 250 $\mu m^2$ to 2 $mm^2$. While the shape of the individual openings may vary, examples of suitable shapes include, but are not limited to: rectilinear shapes, e.g., rectangular, square, triangular, trapezoidal, etc., curvilinear shapes, e.g., circular, cylindrical, oval, etc.; as well as irregular shapes. As the pattern of insulation openings is among the insulated conducting members, a given pattern is made up of openings present in different conductive members. For example, a given pattern of openings may be made of an opening found in each of the different conductive members present in the conductor region of interest, e.g., proximal or distal region. In some instances, a given pattern of openings is made up of a single opening found in each of the different conductive members present in the conductor region of interest, e.g., proximal or distal region. In some instances, a given pattern of openings may include a plurality of openings associated with a given conductive member (e.g., such as a conductive member configured for providing power, to reduce interconnection impedance, etc.), or even exclude a conductive member (e.g., such as for a split configuration, multiple interconnects along the length of the elongated conductor, etc.).

The elongated conductor may include a pattern of insulation openings, e.g., as described above, at just one of the proximal and distal regions. Alternatively, a pattern of insulation openings may be present at each of the proximal and distal regions, such that the elongated structure comprises a first pattern of insulation openings among the insulated conducting members at the proximal region and a second pattern of insulation openings among the insulated conducting members at the distal region. In some instances, the patterns may be encoded to each other, such that, without handling or separately identifying an individual conducting member, a predetermined encoding of the windows of one pattern may be linked to a predetermined encoding of windows on a corresponding pattern (i.e., windows associated with a particular conducing member may be positionally known a priori based on the predetermined encoding). Such a configuration may be advantageous for easy handling of and interconnection with one or more device components (e.g., a flex circuit, a connector, an integrated circuit, a die, a sensor, one or more electrodes, etc.), with the elongated conductor.

Within a given pattern of insulation openings, the arrangement of the individual openings of the pattern may vary greatly, as desired. Such patterns may take on seemingly random or characteristic configurations.

In some instances, the pattern is an axially aligned pattern of insulation openings. By "an axially aligned pattern of insulation openings," is meant that the pattern of openings is positioned substantially along the long axis of the elongated conductor in the region of interest (e.g., a window associated with a particular conducting member may be known by the location of the window with respect to an end of the elongated conductor). FIG. 1A provides an illustration of an axially aligned pattern of insulation openings. As shown in FIG. 1A, a completed connector tip 120a of an elongated body 100 (e.g., a guide wire, a catheter, a lead assembly, etc.), the connector tip 120b exposing the underlying insulating wires 111 and connector contacts 107, and a connector tip 120c exposing the insulating wires 111 and insulated openings 113. As shown in FIG. 1A, proximal end 120a,b,c of elongated conductor 100 includes insulated wires (111) that extend in a packed configuration in a substantially cylindrical assembly of wires. An insulation opening 113 is present along the length of each of the insulated wires 111. As the windows 113 positioned along each of the wires 111 is staggered, the openings are axially arranged along the length of the assembled wires in an axially aligned pattern of insulation openings. As shown in FIG. 1A, the axially aligned pattern of insulation openings 113 is made up of an insulation opening in each of the different wires 111 making up the wire assembly of the of the elongated conductor 100 at the proximal end. In some instances, the wire assembly is surrounded by a sheath 115, e.g., in accordance with embodiments of the present invention. The remaining portion of the elongated conductor 100 is not specifically shown, but the proximal end 120a,b,c is coupled 117 to other regions in of the elongated conductor, in accordance with embodiments of the present invention.

FIG. 1B, provides an illustration of a cross section of the elongated body 100 shown in FIG. 1A as cut along a transverse plane through the elongated body 100 through one of the connector contacts 107. The insulating wires 111 are shown in an assembled arrangement. The insulating wire 111a encoded for the connector contact 107a, is shown with a window 113 formed through the cross section of FIG. 1B.

In some instances, the pattern is a substantially transversely aligned pattern of insulation openings. By "a transversely aligned pattern of insulation openings," is meant that the pattern of openings assumes a substantially linear arrangement across a plurality of two or more conducting members in the conductor region of interest, wherein the linear arrangement is substantially orthogonal, if not orthogonal, to the long axis of the structure made up of the conducting member assembly.

FIG. 1C provides an illustration of a transversely aligned pattern of insulation openings. As shown in FIG. 1C, distal end 110 of elongated conductor 100 includes insulated wires (111) assuming a flat configuration on the surface of a planar support 122. An insulation opening 112 is present in each of the insulated wires 111. The openings are transversely arranged across the assembled wires in a linear arrangement that is orthogonal to the long axis 121 of elongated conductor 100. As shown in FIG. 1C, the transversely aligned pattern of insulation openings 112 is made up of an insulation opening in each of the twelve different wires 111 making up the wire assembly of the of the elongated conductor 100. In some instances, a particular conducting member may be provided with 3 or more insulation openings (e.g., such as to provide charge, current, light, etc. to a plurality of sites along the elongated conductor). As shown in FIG. 1C, the insulation openings 112 are shown in a purely orthogonal arrangement with respect to the long axis 121 of the elongated conductor 100. In some instances, an alternative pattern may be warranted (e.g., so as to form a low profile interconnect with a flexible circuit, an integrated circuit, etc.).

FIG. 1D provides an illustration of a substantially transversely aligned pattern of insulation openings 133 with a staggered pattern 132. It is noted that the staggering of the patterned 132 insulation removal is not required, but can be done to improve the pitch between wires without risking bridging between the contacts during reflow, thermo-compressive fixation, or other type of post formed attachment or assembly process.

FIG. 1E provides an illustration of a transverse aligned pattern of insulation openings as inserted 157 into a sheath 155. In instances, the patterned region of the elongated conductor 151 may be potted within the sheath 155. In instances, the patterned region may be attached to a component, a flexible circuit, an integrated circuit, a connector, etc.

In some instances the elongated structure may include a split configuration and/or a length including a plurality of patterned regions. A split configuration means, a configuration where at least a portion of the conducting members within an elongated structure are separated from the others over a length, such that two or more separated groups of conducting members are present along a cross section over the length. The separated groups may be interfaced with separate connectors, may be interfaced with separate circuits, may be interfaced with the same circuit, may be configured so as to reduce an overall width of the elongate structure over the length, etc.

Figure 2A:
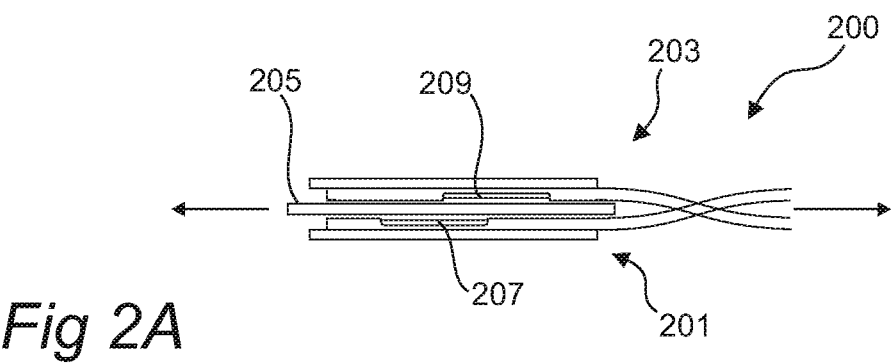
FIGS. 2A-2C provide views of different elongated conductors having different split transversely aligned patterns of insulation openings, in accordance with embodiments of the invention.
Figure 2B:
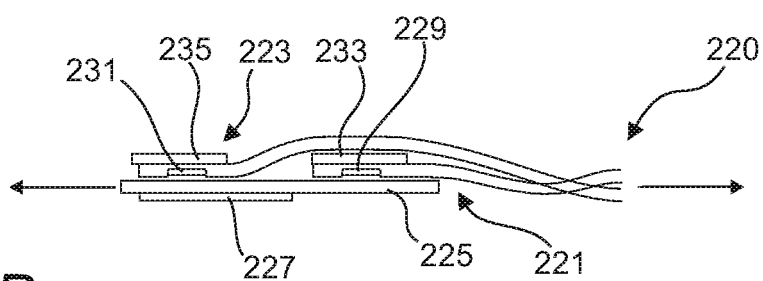
Figure 2C:
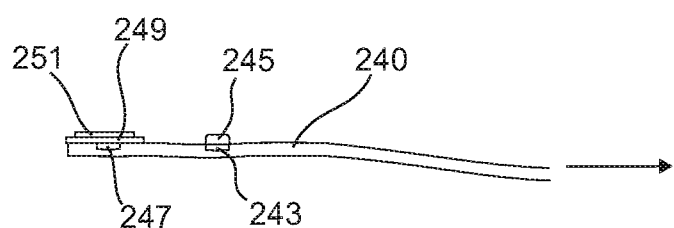

FIGS. 2A-2C provide views of different elongated conductors having different split transversely aligned patterns of insulation openings, in accordance with embodiments of the invention. FIG. 2A provides an illustration of a split-elongated conductor 200 with a split configuration. The split configuration includes a region with two sub-groups 201, 203 of conducting members that are individually patterned for separate attachment to a component 205. In this instance, the component 205 is a flexible circuit, the sub-groups 201, 203 patterned 207, 209 so as to interface with matching patterns on the component 205. The sub-groups 201, 203 are shown supported by corresponding supporting members 207, 209. Such a configuration may be advantageous to provide a highly compact and easily handled approach to coupling an elongated conductor to a component 205. The split configuration may be advantageous to reduce the overall maximum transverse dimension of the elongated conductor in the vicinity of the sub-groups 201, 203. In the embodiment shown in FIG. 2A, the split configuration is configured to provide operable coupling to opposing sides of a component, such as component 205.

FIG. 2B provides an illustration of a split-elongated conductor 220 with a split configuration. The split configuration includes a region with two sub-groups 221, 223 of conducting members that are individually patterned for separate attachment to a component 225. In this instance, the component 225 is an interposer patterned with conducting traces so as to interconnect one or more integrated circuits 227 to the sub-groups 221, 223. The sub-groups 221, 223 are patterned 229, 231 so as to interface with matching patterns on a surface of the component 225. The sub-groups 221, 223 are shown supported by corresponding supporting members 233, 235. Such a configuration may be advantageous to reduce the maximum transverse dimension of the elongated conductor in the vicinity of the component 225. In some instances, the component 225 may include one or more sensors, processors, memory elements, analog to digital circuits, filters, serialization circuits, amplifiers, or the like. In the embodiment shown in FIG. 2B, the split configuration is configured to provide operable coupling to the same side of a component, such as component 225. FIG. 2C provides an illustration of an elongated conductor including a plurality of patterned regions 243, 247, along the length of a sub-group of conducting members 240 therein. A first patterned region 243 is shown coupled with a component 245. In this instance, the component 245 is a passive circuit element (e.g., a bypass capacitor, an inductor, etc.). A second patterned region 247 is shown coupled with a component 249. In this instance, the component 249 is a system in package including a substrate and one or more integrated circuits 251. The patterned regions 245, 247 are separated by a distance, e.g., ranging from 0.01 to 25 mm, such as 1 to 15 mm, such that the flexibility of the overall elongated conductor is not substantially affected by the presence and interconnection with the components 245, 249.

In some instances, the patterned regions may be configured to interface with one or more interposers, inline bypassing circuits or elements, flip chips, silicon dies, sensors, electrodes, etc. The positioning of the patterned regions may be established such that the flexibility of the overall elongated conductor may be maintained during use. Thus the components may be distributed along daisy chains of the patterned regions for maintaining flexibility, etc.

In those instances where the elongated structure includes a pattern of insulation openings at both the distal and proximal regions, the pattern may be the same type of pattern in each of the proximal and distal regions, or the pattern may be a different type of pattern in each of the proximal and distal regions. For example, the elongated conductor may include both a transversely aligned pattern of insulation openings and an axially aligned pattern of insulation openings, where the transversely aligned pattern is present in one of the distal and proximal regions and the axially aligned pattern is present in the other of the distal and proximal regions.

The arrangement of the different conducting members in the elongated conductor may vary, as desired. For example, the different insulated conducting members may assume a wound configuration along at least a portion of the elongated structure. By "wound configuration" is meant that the conducting members are wound about a long axis of the elongated structure, such as the central long axis of the elongated structure. In some instances, each conducting member of the wound configuration assumes a helical configuration. In such instances, the pitch of the helical configuration may vary, ranging in some instances from 0.1 to 1,000 mm, such as 0.25 to 5 mm. In these embodiments, the conducting members assume a wound configuration along at least a portion of the elongated structure. Accordingly, the wound configuration may extend along the complete length of the elongated structure, or along a portion thereof, e.g., 20% or more, 30% or more, 40% or more, 50% or more, 60% or more, 70% or more, 80% or more, up to 99%, such as 95%. As such, in certain of these embodiments the insulated conducting members are not present in a wound configuration along at least a portion of the elongated structure. In some instances, the wound conducting members may be wound around a mandrel so as to form a tubular shape. The mandrel may include a removable sheath such that after winding and fixation of the conducting members to the removable sheath, the mandrel may be removed, leaving a freestanding elongated conductor with a lumen, the lumen walls defined by the removable sheath.

In some embodiments, the different insulated conducting members may assume a braided configuration along at least a portion of the elongated structure. By "braided configuration" is meant that the conducting members are woven or plaited along a length of the elongated structure. In these embodiments, the conducting members assume a braided configuration along at least a portion of the elongated structure. Accordingly, the braided configuration may extend along the complete length of the elongated structure, or along a portion thereof, e.g., 20% or more, 30% or more, 40% or more, 50% or more, 60% or more, 70% or more, 80% or more, up to 99%, such as 95%. As such, in certain of these embodiments the insulated conducting members are not present in a braided configuration along at least a portion of the elongated structure.

In some embodiments, the different insulated conducting members may assume a linear configuration along at least a portion of the elongated structure. By "linear configuration" is meant that the conducting members along the elongated structure are configured in a linear or straight manner along a long axis of the elongated structure, such as the central long axis of the elongated structure. In these embodiments, the conducting members assume a linear configuration along at least a portion of the elongated structure. Accordingly, the linear configuration may extend along the complete length of the elongated structure, or along a portion thereof, e.g., 20% or more, 30% or more, 40% or more, 50% or more, 60% or more, 70% or more, 80% or more, up to 99%, such as 95%. As such, in certain of these embodiments the insulated conducting members are not present in a linear configuration along at least a portion of the elongated structure.

Figure 3A:
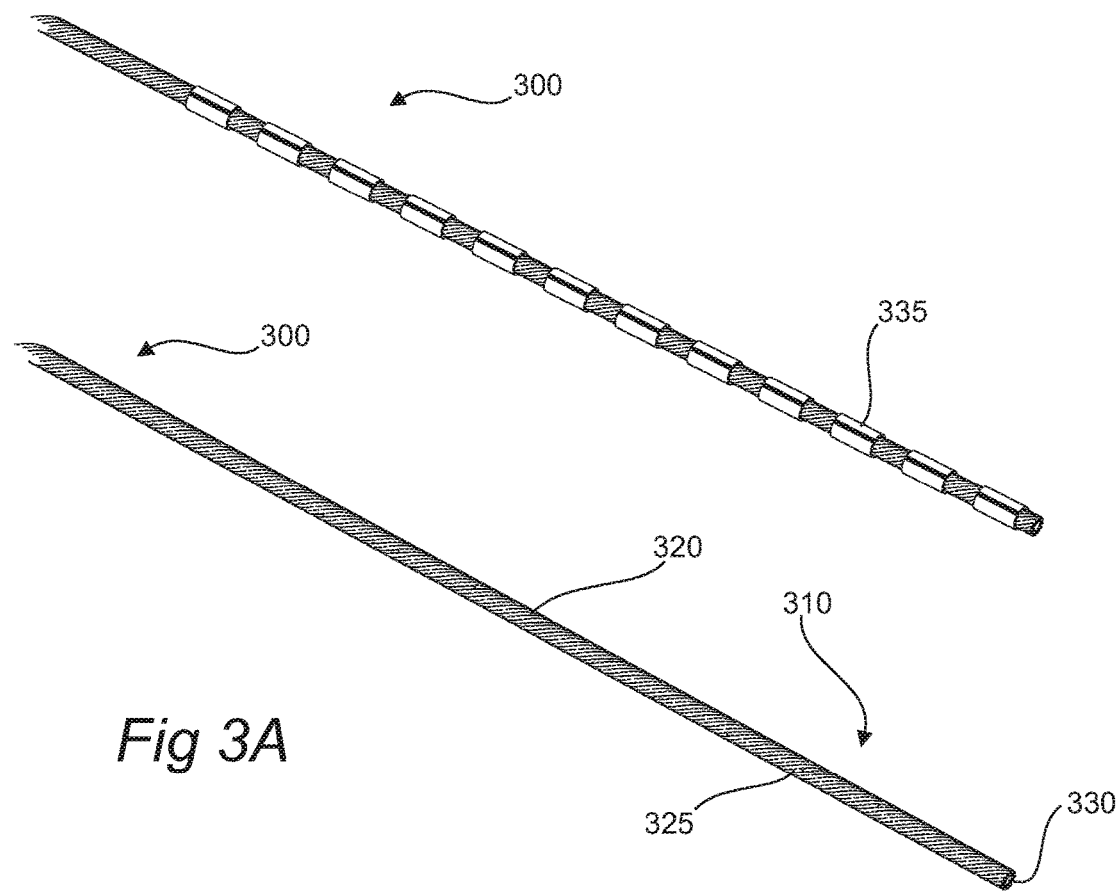
FIG. 3A provides a view of a distal end of an elongated conductor having a transversely aligned pattern of insulation openings and a wound conducting member lumen defining configuration, in accordance with an embodiment of the invention.
Figure 3B:
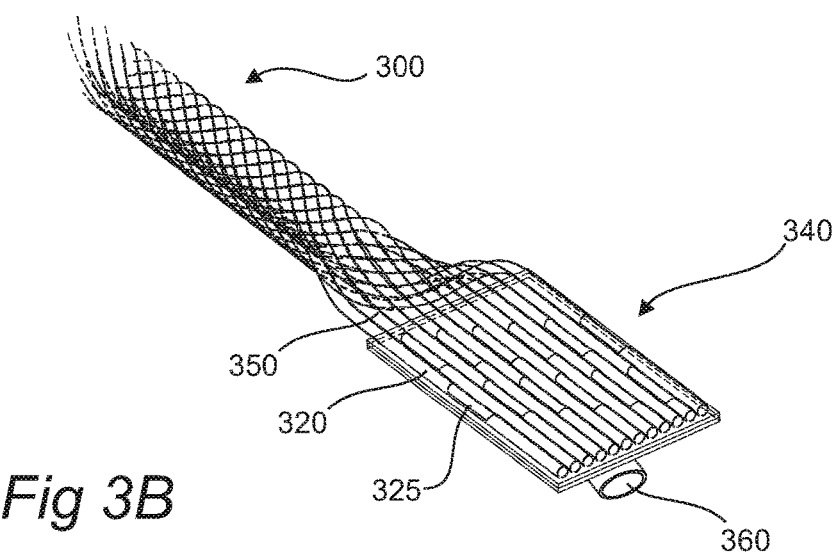
FIG. 3B provides a view of the proximal end of the elongated conductor of FIG. 3A, showing an axially aligned pattern of insulation openings, in accordance with an embodiment of the invention.

In some embodiments, the insulated conducting members are configured to define a lumen along at least a portion of the elongated structure. The term "lumen" is used in its conventional sense to refer to an inner space or cavity, e.g., passageway, which extends along at least a portion of the elongated structure. As the conducting members are configured to define the lumen, they are configured such that, collectively, they define the walls or boundaries of the lumen. In these embodiments, the defined lumen may extend along the entire elongated structure, or only a portion of the elongated structure, e.g., 20% or more, 30% or more, 40% or more, 50% or more, 60% or more, 70% or more, 80% or more, up to 99%, such as 95%. As such, in certain of these embodiments the defined lumen is not present along at least a portion of the elongated structure. FIG. 3A provides a view of the proximal end and FIG. 3B provides a view of the distal end of an elongated conductor in which the conducting members have been wound in manner to produce a lumen extending from the proximal to the distal end. As shown in FIG. 3A, proximal end 310 of elongated conductor 300 includes an assembly of wires 320 wound in a helical fashion that defines a central lumen 330. Each of the wires includes an insulation opening 325, where the collection of insulation openings make up a pattern of axially aligned insulation openings. The insulation openings 325 are coupled with one or more components 335. In this instance, the components 335 may be contact pads on a connector, electrodes, etc. As shown in FIG. 3B, distal end 340 of elongated conductor 300 includes an assembly of wires 320 present in a planar configuration. Each of the wires includes an insulation opening 325, where the collection of insulation openings make up a pattern of transversely aligned insulation openings. Also shown are regions 350 where the conducting members are not fixed, e.g., to provide strain relief. FIG. 3B also shows mandrel 360 which is used during fabrication of the structure as a guide about which the conducting members are wound to produce the central lumen. In some instances, the mandrel 360 may include a removable part, such that after formation and fixation of the elongated conductor 300, the mandrel 360, or a portion thereof may be removed so as to form a lumen there through.

Figure 3C:
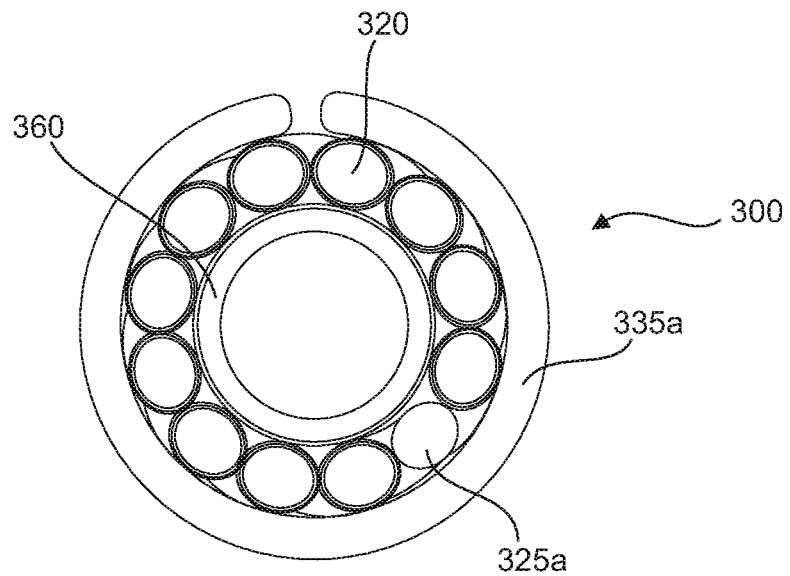
FIG. 3C provides a view of a cross section of the proximal end of the elongated conductor of FIG. 3B, in accordance with an embodiment of the invention.

FIG. 3C provides a cross sectional view of the proximal end of the elongated conductor 300 shown in FIG. 3A. The insulated wires 325 are shown in a wound pattern around the mandrel 360. The cross sectional view passes through a component 335a adjacent to an insulation window 325a, meant for coupling thereto.

Figure 3D:
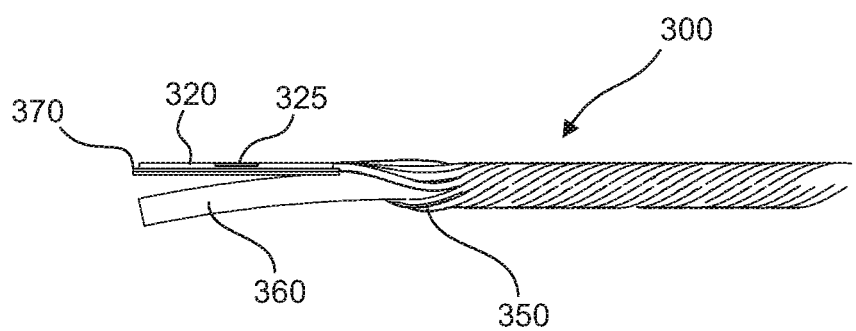
FIG. 3D provides an alternative view of the distal end of the elongated conductor of FIG. 3A, in accordance with an embodiment of the invention.

FIG. 3D provides an alternative view of the distal end of the elongated conductor 300 shown in FIG. 3A. The mandrel 360 is shown passing under the patterned region. The insulated wires 320 are supported by a substrate 370. There is a patterned region, a region where the wires are not coupled together 350, and a region where they are wound about the mandrel 360.

In some instances, the lumen may be suitable for passing a fluid along the length of the elongated conductor (e.g., for purposes of heating/cooling, delivery of a coolant, delivery of a drug, a medication, a biological sample, etc.). While the dimensions of the lumen may vary, in some instances the lumen has a diameter ranging from 0.025 to 20.0 mm, such as 0.10 to 5.0 mm and including 0.10 to 1.0 mm.

In some instances, the lumen may be occupied by one or more internal components. For example, the lumen may be occupied by one or more internal conducting members, which conducting member(s) may occupy the entire lumen or a portion thereof. In one instance of such an embodiment, the elongated conductor includes a central insulated conductor surrounded by a plurality of peripheral insulated conductors, which peripheral conductors may be wound about the central conductor, braided about the central conductor, or linearly extend along the central conductor.

Where desired, the insulated conducting members may be present in a sheath. The term "sheath" is employed in its conventional sense to refer to an enveloping tubular structure. The sheath, when present, may extend along the entire elongated structure, or only a portion of the elongated structure, e.g., 20% or more, 30% or more, 40% or more, 50% or more, 60% or more, 70% or more, 80% or more, up to 99%, such as 95%. As such, in certain of these embodiments the sheath is not present along at least a portion of the elongated structure. The sheath may be fabricated from any convenient material, as desired. In some instances, the sheath is fabricated from a conductive material. Conductive materials of interest for the sheath include, but are not limited to: a thermally conductive material, an optically conductive material, an electrically conductive material, a conductive polymer, a conducting composite, a metal, a precious metal, a conducting alloy, silver, copper, platinum, palladium, steel, carbon, stainless steel, an alloy thereof, a composite thereof, and the like. In some instances, the sheath is fabricated from an insulating material. Insulating materials of interest for the sheath include, but are not limited to: a thermally insulating material, an optically reflective material, an electrically insulating material, a polymer, a thermoset polymer, a thermoplastic polymer, high strength fibers, a ceramic loaded polymer, a low dielectric polymer, a high field strength polymer, a composite thereof, and the like. In some instances, the sheath is fabricated from a water-impermeable material, by which is meant that the sheath inhibits passage of water from one side of the sheet to the other. In some instances, the sheath is fabricated from a water retaining material (e.g., a hygroscopic material, a hydrogel, etc.), such that the sheath may provide a lubricating surface for the elongated conductor when placed within an aqueous environment.

Where desired, the insulated conducting members of at least one of the proximal and distal regions are stably associated with a substrate. For example, in a region where the conducting members assume a substantially planar (e.g., ribbon) configuration, the conducting members may be stably associated with a substrate, e.g., in the form of a planar support. The planar support may be fabricated from any convenient material, e.g., a metal, a ceramic, a cermet, a silicon interposer, a radiopaque material, an adhesive tape, a b-stage able adhesive tape, and the like. In some instances, the planar support may provide an interconnect function for one or more of the conducting members. In some instances, the planar support may provide an insulating property, a structural reinforcement, a precision planarization function, a conducting property (e.g., acting as a heat sink), or the like. The dimensions of the planar support may vary, where in some instances the support has a surface area contacted by conducting members that ranges from 100 $\mu m^2$ to 100 $mm^2$, such as 1000 $\mu m^2$ to 5 $mm^2$ and including 0.5 to 1.5 $mm^2$.

As indicated above, the insulated conducting members of the elongated conductors are made up of at least a conducting core present in an insulating coating. As summarized above, the elongated conductors may be configured to conduct different entities, e.g., light, heat, electric current, etc. Where the conductors are configured to convey electric current, i.e., they are electrically conductive, the conductive core may be fabricated from any convenient electrically conductive material. Electrically conductive materials of interest include, but are not limited to: metals, e.g., copper, silver, gold, platinum, palladium, titanium, tantalum, etc., alloys, e.g., stainless steel, silver copper alloys, shape memory alloys, e.g., Nitinol™ shape memory alloys, high performance alloys, beryllium copper alloys, titanium alloys, nickel titanium alloys, corrosion resistant alloys, cobalt-chromium-nickel-molybdenum-iron alloys, shape memory materials, core shell composite structures, carbons, carbides, composites thereof, alloys thereof, and the like.

The insulating coating surrounding the conductive core may be fabricated from any convenient insulating material. In some instances, this insulating coating is fabricated from a thermostable material (i.e. a substantially thermally stable material with respect to processing and usage conditions expected by the elongated conductor). Thermostable materials that may be employed include materials having a melting temperature that is 20° C. or greater, such as 30° C. or greater, including 40° C. or greater, than the melting temperature of one or more thermoplastic components of the conductor, such as binding components, e.g., as described in greater detail below. Thermostable materials of interest include, but are not limited to: a polymer, a ceramic, an oxide, a thermoset polymer, a high melting temperature polymer, a chemically resistant polymer, a polyimide, a polyamide, a fluoropolymer, PTFE, a polyurethane, a polyolefin, a polyetheretherketone, a silicone, a cross-linked polymer, composites thereof, glass reinforced versions thereof, and the like.

Within an elongated conductor, the various conductive members may be stably associated with each other using any convenient approach. In some instances, the various conductive members are fixed relative to each other by a thermoplastic material which, during fabrication of the elongated conductor, (e.g., as described in greater detail below) has been molded in manner sufficient so to occupy the spaces between the conductive members and fix the conductive members relative to each other, e.g., as shown in FIG. 4, described in greater detail below. Thermoplastic materials of interest include, but are not limited to: a plastic, a chemically susceptible polymer, a polyurethane, a polyvinyl chloride, a poly butyral, an epoxy, a polyester, a polyamide, Dacron, composites thereof, and the like.

As summarized above, the dimensions of the elongated conductors may vary. In some instances, the elongated conductors are dimensioned to be positioned be positioned in mammalian vasculature. The reference vasculature may be from a variety of different mammals. Mammals of interest include carnivores (e.g., dogs and cats), rodentia (e.g., mice, guinea pigs, and rats), and primates (e.g., humans, chimpanzees, and monkeys). In some embodiments, the mammal is a human. The term "human" may include human subjects of both genders and at any stage of development (e.g., fetal, neonates, infant, juvenile, adolescent, and adult), where in certain embodiments the human subject is a juvenile, adolescent or adult. While the dimensions of a given elongated conductor of the invention may vary, in some instances the elongated conductor has a length ranging from 5 to 4,000 mm, such as 50 to 2,000 mm, and an outer diameter ranging from 5 $\mu m$ to 10 mm, such as 15 $\mu m$ to 7.5 mm, including 25 $\mu m$ to 5 mm, where in some instances the outer diameter is very small, e.g., 5 $\mu m$ to 500 $\mu m$, such as 10 $\mu m$ to 350 $\mu m$, including 15 $\mu m$ to 300 $\mu m$.

Where desired, the insulated conductors of at least one of the proximal and distal regions assume a split configuration, e.g., as shown in FIGS. 2A-2C.

As indicated above, the elongated conductors may include one or more shielding components, where such shielding components may vary. Examples of such shielding components include, but are not limited to: sheaths, such as described above; subgroupings of one or more electrically conducting members (e.g., wires), which may be arranged around the outer periphery of the elongated conductor (e.g., in a wound or braided configuration) or may be present in an internal location of the elongated conductor, e.g., one of the internal conducting wires is connected to another component, e.g., the guidewire, for either a floating shield or a grounded shield); a conductive insulating layer of one or more conducting members; a binding layer of the elongated conductor; etc.

As indicated above and detailed further below, the elongated conductor may have a structure that provides for a controlled impedance, at least along a portion of the conductor length, e.g., where the controlled impedance may be viewed as a known fixed impedance/unit length. The structure and interaction of components in the elongated conductor can be chosen to provide for a desired impedance along at least a portion of, if not all of, the length of the elongated conductor, which impedance may be tailored to the intended use of the device in which the elongated conductor is to be present. For example, the impedance of the conductor and/or sub-portions thereof may be chosen depending on the types of signals that are to be conveyed along the conductor, e.g., cardiac EPS, neuro, brain, etc., and may be selected to work optimally with communications units, e.g., RF units, at an end of the conductor.

The elongated conductor may, where desired, be configured to function as a guidewire. In such instances, the elongated conductor is configured as a thin, usually flexible wire that can be inserted into a confined or tortuous space to act as a guide for subsequent insertion of a stiffer or bulkier instrument. In such instances, the elongated conductor may include variable mechanical compliance to make the distal tip not only a contact point, but also good as a steering mechanism/function, e.g., as is present in standard guidewires. Where desired, the distal end of the conductor may be shapeable, e.g., as in the bending tips of guidewires currently employed for specific anatomic access sites.

In some instances, the elongated conductor may include one or more radiopaque regions. By radiopaque region is meant that a domain or area of the elongated conductor that is opaque to one or another form of radiation, such as X-rays. Radiopaque objects block radiation rather than allow it to pass through. Any convenient radiopaque material may be present in the radiopaque region(s), where materials of interest include, but are not limited to, metals, e.g., tantalum, platinum, palladium, barium sulfate, bismuth sub carbonate, bismuth oxychloride, bismuth trioxide, stainless steel, Nitinol™ shape memory alloys, platinum/iridium, tungsten, filled polymers thereof, a radiopaque polymer, a composite material, an alloy thereof, a composite thereof, and the like. The radiopaque region may vary in configuration, and may limited to one or more portions of the elongated conductor, e.g., where the elongated conductor includes one or more marker bands made up of a radiopaque material.

The elongated conductors having been generally described, specific examples of such conductors are reviewed in connection with various figures. FIGS. 4A and 4B provide views of complete elongated conductors. FIG. 4A provides a view of an elongated conductor 400 having a proximal region 410 with an axially aligned pattern of insulation openings and a distal region 420 of transversely aligned insulation openings. The elongated conductor 400 illustrated in FIG. 4A may be viewed as one that axially encoded at the proximal end and transversely encoded at the distal end. FIG. 4B provides a view of another elongated conductor according to any embodiment of the invention. The elongated conductor 450 includes proximal end 460 and distal end 470, where the body of the elongated conductor is covered by a sheath 475. In this embodiment, the sheath (e.g., an ultrathin hypotube initial structure) can provide a complete shield, and effectively form a Faraday cage around the entire assembly. Also, the wires themselves are now hermetically sealed within the device, and thus can be formed from considerably lower cost materials than would be the case if they could be exposed to the surrounding tissues.

FIGS. 5A-5C provide schematics of elongate conductors demonstrating a range of end interconnection options, in accordance with embodiments of the invention. FIG. 5A provides a schematic of an elongate conductor 500 demonstrating different proximally 505 and distally 510 encoded regions coupled by an elongate region 515. The individual conducting members within the elongate conductor 500 may be encoded in the regions 505, 510 so as to provide a simple handling and robust interconnect feature to components (not explicitly shown), configured to interface with each region 505, 510. The elongate region 515 may be configured such that the individual conducting members therein are fixed relative to each other, so as to enhance mechanical robustness of the assembly during fabrication, handling, etc.

FIG. 5B provides a schematic illustration of an elongated conductor 520 including a proximal 525, and two distal 530, 535 encoded regions coupled by a plurality of split elongate regions 540, 545 and a unified elongate region 550. The proximal 525 and distal 530, 535 encoded regions may be coupled such that a single proximal component (e.g., a connector, a coupling, etc.) may interface with two components (not explicitly shown) coupled to the distally encoded regions 530, 535.

FIG. 5C provides a schematic illustration of an elongated conductor 560 including multiple proximal 561, 563, and multiple distal 565, 566, 567, 569 encoded regions coupled by a plurality of distally split regions 577, 579, 581, 583 and proximally split regions 573, 575 and a unified elongate region 571. The assembly is suitable for a more complex device, wherein a plurality of connectors (e.g., fluid connectors, electrical connectors, optical couplings, etc.) may be coupled with a plurality of effectors (e.g., fluid delivery elements, integrated circuits, Bragg gratings, optical interfaces, etc.). Also shown is a series of split regions 577, 579 illustrating a daisy chained configuration of encoded regions 567, 569 wherein individual conducting elements within the split regions 577, 579 may couple to components in the vicinity of both encoded regions 567, 569.

Figure 6A:
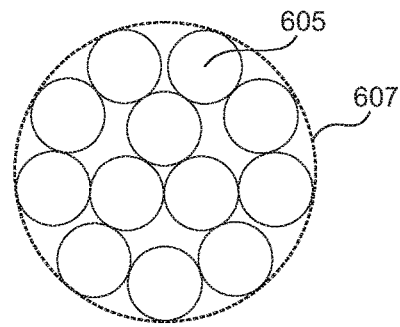
FIGS. 6A-6D provide illustrations of elongate conductors with high packing density and specialized conductor arrangements, in accordance with embodiments of the invention.

FIGS. 6A-6D provide illustrations of elongated conductors with high packing density and specialized conductor arrangements, in accordance with embodiments of the invention. FIG. 6A provides an illustration of the cross section of an elongated conductor including 12 conducting members 605 tightly packed into a circular area 607. The packing density of this arrangement as arranged is approximately 0.74 in the shown configuration and will generally be slightly higher after a fixation procedure as described herein.

Figure 6B:
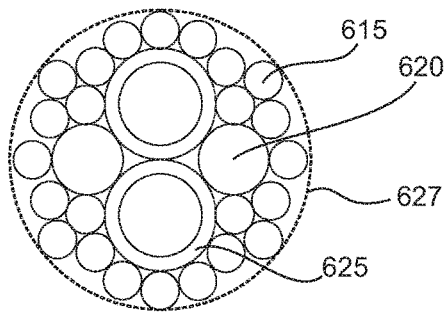

FIG. 6B provides an illustration of an elongated conductor including 24 conducting members 615 with a first diameter, 2 conducting members 620 with a second diameter and two fluid conducting members 625 with a third diameter packed into a circular area 627. The packing density of this arrangement as arranged is approximately 0.77 in the shown configuration and will generally be slightly higher after a fixation procedure as described herein. Such a configuration may be advantageous for providing a combination of sensory signals (i.e., such as via the first conducting members 615), power signals (i.e., such as via the second conducting members 620), and a fluid (e.g., a coolant, a medicament, etc.) such as via the fluid conducting members 625 in a highly compact and space optimized structure.

Figure 6C:
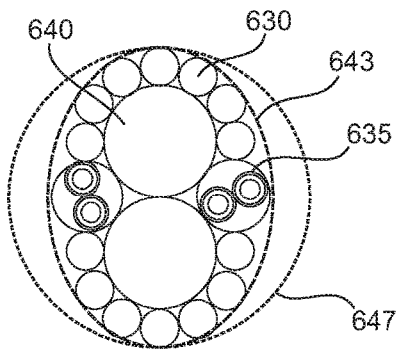

FIG. 6C provides an illustration of an elongated conductor including 14 conducting members 630 with a first diameter, 2 twisted pair based conducting members 635 with a second effective diameter and 2 larger conducting members 640 with a third diameter packed into an elliptical area 643. The packing density of this arrangement as arranged is approximately 0.83 in the shown configuration based on the elliptical area 643, and 0.62 based on the equivalent circular area 647 and will generally be slightly higher after a fixation procedure as described herein. Such an arrangement may be advantageous for providing a combination of sensory signals (e.g., such as via the first conducting members 630), power signals (e.g., such as via the second conducting members 640), and sensitive high speed signals (e.g., via the twisted pair conducting members 635) in a highly compact and space optimized structure.

Figure 6D:
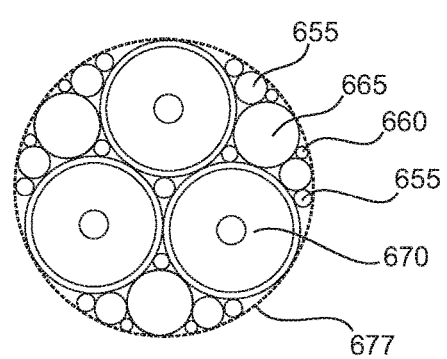

FIG. 6D provides an illustration of an elongated conductor including 6 conducting members 650 with a first diameter, 16 reinforcing fibers 655, 660, three conducting members 665 with a second effective diameter, and 3 larger coaxially oriented conducting members 670 with a third diameter packed into a circular area 677. The packing density of this arrangement as arranged is approximately 0.917 in the shown configuration based circular area 677 and will generally be slightly higher after a fixation procedure as described herein. Such an arrangement may be advantageous for providing a combination of sensory signals (e.g., such as via the first conducting members 665), power signals (e.g., such as via the second conducting members 665), and RF power signals (e.g., via coaxially conducting members 670) in a highly compact and space optimized structure.

In some instances, one or more of the members may include an actuator (e.g., a pull-able fiber used to actuate, bend, tilt, orient, the elongated structure, during use).

Methods of Making

Also provided are methods of making elongated conductors, e.g., as described above. Aspects of the methods include aligning two or more insulated conducting members in an elongated configuration having a proximal region and a distal region; and producing a pattern of insulation openings among the insulated conducting members at one or both of the proximal and distal regions. The methods further include, either after or before pattern production, fixing the relative position of the two or more insulated conducting members along at least a portion of the elongated conductor. Each of these steps of the fabrication methods is now reviewed in greater detail.

In practicing methods of the invention, two or more insulated conducting members may be aligned in an elongated configuration having a proximal region and a distal region using any convenient protocol. As indicated above, the number of wires in a given elongated conductor may vary, where in some instances the number ranges from 2 to 100,000, such as 2 to 500, e.g., 5 to 250, including 5 to 100. In some instances, the conducting members are aligned by extending them lengthwise next to each other. Where desired, tension may be applied at one or both ends of the conducting members in order to provide for consistent linear alignment. Where desired, an aligner, e.g., a guide, microfixture, etc., that holds the individual conducting members at predetermined distances from each other may be employed. The distances between the conducting members may vary, ranging in some instances from 0.001 to 10 mm, such as 0.1 to 2 mm. Where an aligner, such as a microfixture, is employed, the conducting members may be threaded into the aligner in a continuous manner, which each conducting member being fed to the aligner from a separate source, e.g., spool. Embodiments of this aligning step may be performed in pseudo continuous fashion with a dedicated machine, as desired. The aligned conducting members may assume any desired three-dimensional configuration, e.g., planar, tubular, etc., as desired, where in some instances the aligned conducting members will assume a planar configuration during a first operation and an alternative configuration during a following operation. Optionally, the distal and proximal regions of the aligned conducting members may be fixed relative to each other, e.g., may be gripped, pre-bonded, etc., at this point to form a desired end construction without the need for human intervention.

As summarized above, methods of fabricating the elongated conductors further include producing a pattern of insulation openings among the insulated conducting members at one or both of the proximal and distal regions. As such, the methods may include producing a pattern of insulation openings at only one of the proximal and distal regions, producing a pattern of insulation openings at both of the proximal and distal regions, or producing a plurality of patterns along the length thereof, and/or along split regions thereof. As such, in some instances the method includes producing a first pattern of insulation openings among the insulated conducting members at the proximal region and a second pattern of insulation openings among the insulated conducting members at the distal region. As described above, the pattern of insulation openings may assume a variety of configurations, e.g., depending on whether the desired pattern in the final elongated conductor, which may also vary as described above, e.g., it may be transversely aligned, axially aligned, patterned over an area, daisy chained along the elongated conductor, etc. The pattern that is produced in aligned conducting members may be one that is chosen in view of subsequent manipulation of the conducting members (e.g., as described in greater detail below) so as to provide for the desired pattern in the final product. For example, where the desired pattern in the final elongated conductor is an axially aligned pattern, and initial pattern produced in the aligned conducting members may be one that gives rise to the desired axially aligned pattern following winding or wrapping of the conducting members, e.g., as described in greater detail below. In some instances, the method includes producing first and second patterns of insulation openings in the proximal and distal regions that will give rise to an elongated conducting having both a transversely aligned pattern of insulation openings and an axially aligned pattern of insulation openings.

The pattern of insulation openings in the proximal and/or distal regions of the aligned elongated conductors may be produced using any convenient protocol. Of interest are material removal processes, e.g., laser removal processes, chemical removal processes, plasma removal processes, etc. In some instances, laser removal protocols are employed, where examples of such protocols include those that employ UV, $CO_2$ and YAG lasers. Protocols that may be employed also include masked removal protocols, such as masked plasma removal and masked flame removal protocols. For larger conducting members, more traditional insulation removal approaches can be used, such as abrasion, etc. For smaller conducting members, non-contact insulation removal may be employed, e.g., to preserve the delicate nature of the conducting members. In high volume production applications, the insulation of the aligned conducting members may be removed with an imaged, large area UV laser beam (e.g., from an excimer laser, such that each of the windows in the insulation are opened substantially simultaneously). In this way, bulk insulation removal can occur at a pace of several units per second. The pattern may be adjusted so as to make the wires suitable for interfacing with a flexible circuit (see below), an interposer, a sensor, a silicon die, a flip chip packaged element, an optical component, a Bragg grating, an optimized energy transfer structure, for forming a coaxial connector (see below), etc.

As indicated above, a third step employed in production of the elongated conductors is to fix the relative position of the two or more insulated conducting members along at least a portion of the elongated conductor. As reviewed above, by fixing is meant stably associating the aligned conducting members, such that the conducting members in the region of fixation do not move relative to each other. As also reviewed above, the aligned conducting members may be fixed along their entire length, or there may be one or more regions along the length of the aligned conductors that is not fixed, e.g., to provide for strain relief. As also indicated above, fixation of the aligned conductors may be done prior to or after production of the pattern(s) of insulation openings. As such, in some instances the aligned conducting members are fixed prior to production of the pattern(s) of insulation openings. In other instances, the aligned conducting members are fixed after production of the pattern(s) of insulation openings.

The aligned conducting members may be fixed using any convenient protocol. For example, the aligned conducting members may be mechanically fixed relative to each other, e.g., using any convention mechanical fixation component, such as but not limited to: a cuff, sheath, etc. Alternatively, a binding material may be employed to fix the different elongated conducting members relative to each other. The binding material may be any of a number of different materials, such as an adhesive, a phase change material, a b-stage able adhesive, a photo crosslink able material, etc. In some instances, the binding material is provided as an outer layer of the elongated conducting members, which binding material is employed during the fabrication process to produce the desired elongated conductors with fixed conducting members.

An example of such an embodiment is where the insulated conducting members include an insulation material that is present about the conducting core and a second binding material that is formed about the insulation material, such that the conducting member has a conducting core with an inner concentric insulation material and an outer concentric binding material. The thickness of the insulating material may vary, as desired, ranging in some instances from 0.25 to 500 µm, such as 1 to 50 µm and including 5 to 15 µm, where in some instances the thickness is sufficient to electrically isolate one conducting member from another in the finished assembly. The insulation thickness and material composition may be designed so as to maintain the desired controlled impedance between one or more conducting members, e.g., wires, in the assembly. This insulation may be formulated so as to not substantially change state during the bonding process. A variety of different materials may be employed for the insulation, where materials of interest include, but are not limited to: a thermally insulating material, an optically reflective material, an electrically insulating material, a polymer, a thermoset polymer, a thermoplastic polymer, high strength fibers, a ceramic loaded polymer, a low dielectric polymer, a high field strength polymer, a composite thereof, a plastic, a chemically susceptible polymer, a polyurethane, a polyvinyl chloride, a poly butyral, an epoxy, a polyester, a polyamide, Dacron, composites thereof, a polymer, a ceramic, an oxide, a thermoset polymer, a high melting temperature polymer, a chemically resistant polymer, a polyimide, a polyamide, a fluoropolymer, PTFE, a polyolefin, a polyetheretherketone, a silicone, a cross-linked polymer, composites thereof, glass reinforced versions thereof, a radiopaque polymer, a polymer composite including tantalum, platinum, palladium, barium sulfate, bismuth sub carbonate, bismuth oxychloride, bismuth trioxide, stainless steel, nitinol, platinum/iridium, or tungsten, a composite material, an alloy thereof, and the like.

In some instances, the insulating and/or binding layer may include a piezoresistive and/or piezoelectric material such that one or more electrical properties of the elongated conductor substantially change during flexure, pressure application, contact load along a region of the elongated conductor, etc. In other words, the elongated conductor includes a piezo component, where the piezo component may be a piezoresistive component or a piezoelectric component. Such components may be used for a variety of different purposes, e.g., to detect tip flexure and force directly by looking at changes in the inter-wire impedance changes of the overall assembly (which finds use in monitoring movement feedback and artifact removal, wall pressure application, etc.) When the piezo component is a piezo material incorporated into a layer of the conductor, such as an insulating and/or binding layer, the piezo material may extend along the entire length of the conductor or only a portion thereof, as desired. In some instances, the insulating and/or binding layer may include a region of a carbonyl metal—elastomer composite (such as a carbonyl nickel—silicone composite), such that mechanical stress applied to the structure in the vicinity of the carbonyl metal—elastomer composite would substantially change the electrical properties thereof.

The outer concentric binding material may vary widely, so long as it can serve to bind the conducting members in a stable configuration in the final elongated conductor. In some instances, the binding material is one that can be transitioned between adhesive and non-adhesive states in response to an applied stimulus. For example, the outer binding material may be one that can be thermally, optically, and/or chemically, altered as to form a tacky, softened, or adhesive state, which state may be employed to initial secure the aligned conducting members to each other in the desired configuration. This state may be a temporary state to provide a temporal window for processing the wires into the assembly. Following attainment of the desired final arrangement of the conducting members in the elongated structure, the state of the binding material may be returned to the non-tacky, softened, or adhesive state so as to provide a stable, durable association of the conducting members on the elongated conductor. A variety of different materials may be employed as the binding material, where materials of interest include both conducting materials and non-conducting materials. Conducting materials of interest include, but are not limited to: inherently conducting polymers, metal frit filled polymer composites, a silver loaded thermoplastic polymer composite, and the like. Non-conducting materials include, but are not limited to: a plastic, a chemically susceptible polymer, a polyurethane, a polyvinyl chloride, a poly butyral, an epoxy, a polyester, a polyamide, Dacron, composites thereof, and the like. In some instances, the binding material is a thermoplastic material, which material becomes tacky upon application of heat, e.g., at a temperature ranging from 35 to 500° C., such as 90 to 230° C., and then returns to a non-tacky state upon cooling, e.g., to room temperature. In such embodiments, the aligned conducting members may be heated to a sufficient temperature such that the outer thermoplastic binding materials of the individual conducting members become tacky and merge with each other. Following this heating step, the resultant structure is allowed cool in a manner such that the merged binding materials of the various conducting members have merged into a stable, monolithic structure which serves to fix the various conducting members relative to each other.

Figure 7A:
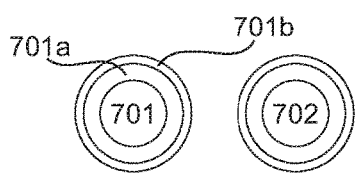
FIGS. 7A-7C provide an illustration of a fixing step of a method of fabricating at least a portion of an elongate conductor with a controlled inter-element pitch, in accordance with an embodiment of the invention.
Figure 7B:
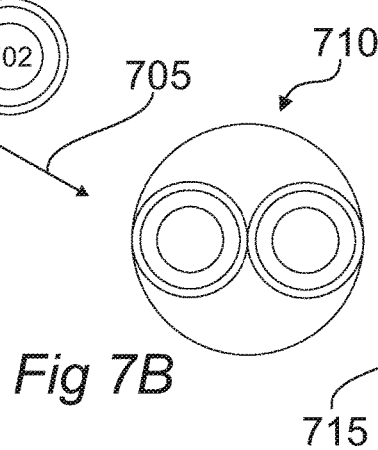
Figure 7C:
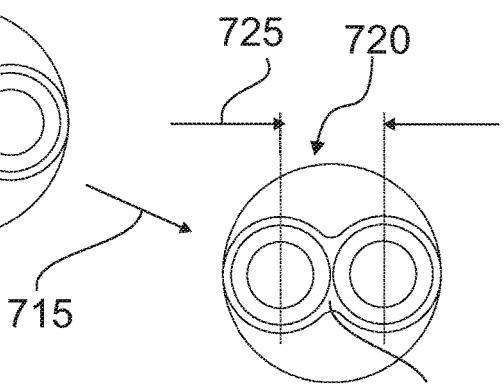

An example of this procedure is illustrated schematically in FIGS. 7A-7C. As shown in FIG. 7A, an initial non-fixed assembly of linearly aligned wires 701 to 702 are is produced. Each of the wires includes an inner concentric insulating layer, e.g., 701*a*, and an outer concentric layer of a thermoplastic binding material, e.g., 701*b*. The wires 701, 702 are brought together 705 to form a tightly arranged assembly 710, as shown in FIG. 7B. For fixing the assembly, heat is applied 715 to produce the a fixed assembly 720 as shown in FIG. 7C which is made up of wires 701 to 702, where the outer binding material layers of each wire have merged to produce a binding structure 701*b*' which serves to fix the assembly of wires together into the assembly. Although not required, the pitch 725 between the wires 701, 702 in the fixed assembly 720 may be defined primarily by the diameters of the wires 701, 702, and the thickness of the corresponding concentric insulating layers 701*a*, while the strength with which the assembly is held together is primarily defined by the corresponding binding materials 701*b*. Together, FIGS. 7A-7C provide an illustration of a fixing step of a method of fabricating at least a portion of an elongate conductor with a controlled inter-element pitch, in accordance with an embodiment of the invention.

Prior to the fixation step, e.g., as described above, the conducting members may be manipulated to achieve a desired configuration. For example, the conducting members may be wound, braided, segmented, split into separate sub-groups (e.g., subgroups manipulated separately from other members of the group, etc.) or otherwise manipulated in order to produce a desired configuration of conducting members in the final elongated structure. Any convenient protocol for manipulating the conducting members may be employed. For example, where the conducting members assume a wound configuration in the final elongated conductor, the aligned conducting members may be twisted or turned about each other to provide the final desired configuration. The conducting members may be wound together, either in initial pairs, groups, etc. or all together as a group, so as to form a tightly bound assembly, as desired. Where the final elongated conductor includes a lumen, e.g., as described above, the conducting members may be wound about a mandrel or analogous structure, which may then be separated from the conducting members following fixation to provide the desired elongated conducting member having a lumen. For example, elongated conductors may be configured to provide for fluid delivery along at least a portion of their length in combination with the electrical/optical interconnections. In these instances, a central lumen can be integrated into the elongated conductor by employing a forming mandrel over which the winding process of the conducting members may be performed. After winding, the final mandrel may be removed so as to form the lumen (with or without an associated sheath, as desired). At the ends, the same connectors can be formed, they may just be held during the winding process in order to ensure the mandrel does not get in the way during formation of the final assembly. The hollow center may include a tube, which may be extended beyond the ends so as to provide for fluid coupling at either side, in addition to the associated electrical/optical couplings. Optionally, once wound together, the conducting members may undergo a stress relief, a rewind procedure, etc., as desired.

As reviewed above, the elongated conductors may include a sheath. To produce elongated conductors of these embodiments, a fixed assembly of aligned conducting members, e.g., as described above, may be inserted into a sheath. As reviewed above, the sheath may be fabricated from a conducting or non-conducting material, as desired. Where the final desired elongated conductor includes an outer sheath of narrow diameter, e.g., a sheath having an outer diameter ranging from 0.025 to 20.0 mm, such as 0.10 to 5.0 mm and including 0.10 to 1.0 mm, a sequential sheath insertion protocol may be employed to position the fixed conductive member assembly into the final desired sheath. Sequential sheath insertion protocols are ones that include inserting the aligned insulating conductors into a first sheath and then inserting a second sheath into the first sheath between the first sheath and the insulated conducting members, where the second sheath has an outer diameter that is shorter than the inner diameter of the first sheath, e.g., by a value of 0.1 to 500 mm, such as 0.1 to 10 mm, and then separating the first sheath from the remainder of the assembly (made up of the second sheath and insulating conducting members); where the process may be iterated as desired to obtain the desired final elongated conductor having a sheath of desired outer diameter. In an example of such fabrication embodiment, a fixed aligned conducting member assembly, e.g., as described above, is threaded through a relatively larger initial sheath such that it will not buckle during the insertion process. While the dimensions of this initial sheath may vary, in some instances this initial sheath has an inner diameter ranging from 0.05 to 5 mm, such as 0.05 to 0.5 mm, and an outer diameter ranging from 0.075 to 6 mm, such as 0.075 to 0.6 mm. Next, sequentially smaller dimensioned sheaths are threaded through the larger sheath such that the conductor assembly is constrained from buckling (i.e., the buckling distance is reduced such that the conductor assembly has nowhere to retreat to during the passage process). In some instances, the outer diameter of each successively smaller dimensioned sheath is 0.02 to 4.9 mm, such 0.02 to 0.49 mm shorter than the inner diameter of the preceding sheath employed in the protocol. The outer sheath is then removed and the process is repeated as desired. In this protocol, the process is continued with smaller and smaller sheaths until the final desired sheath is in-place. In this way, elongated conductors may be fabricated in which the overall inner diameter of the sheath is just barely larger than the overall outer diameter of the conducting member assembly present in the sheath. While the difference in these diameters may vary, in some instances, the difference ranges from 0.01 to 0.1 mm, such as 0.01 to 0.05 mm.

In some instances, the methods may include stably associating one or both of the proximal and distal regions of the aligned conducting members with a substrate, such as a planar support, e.g., as described above. When associated with a substrate, the end region and the substrate may be stably associated with each other prior to or after fixation of the elongated members, e.g., as described above. As described above, "stably associating" means fixing the relative position of the end region and the substrate such that they two associated components do not move relative to each other under normal conditions of use. Stable association may be achieved using any convenient protocol, e.g., via use of adhesives, press fit structures, etc.

In some instances (e.g., in the production of various devices, such as described below), the methods may include conductively, e.g., electrically, coupling one or more of the conducting members of the elongated structure with one or more other components, e.g., a connector, an effector, etc., at one or both of the distal and proximal regions of the elongated conductor. The components may be a variety of different types of components depending on their function in the overall device in which the elongated conductor is employed, where examples of the types of components that may be present include, but are not limited to: a wafer, a microcircuit, a flexible substrate, an interposer, a flexible microcircuit, a double sided microcircuit, a flip chip integrated circuit, a contact pad, an annular contact pad, a ringlet of a conducting material, an actuator, a pull cable, a pull cable fixation point, a sensor, a thermocouple, a pH sensor, a pressure sensor, a flow sensor, a valve, a port, an electromechanical microvalve, a manifold, a microfluidic element, an electromagnetic microfluidic element, an electrochemical sensor, a silicon circuit, a CMOS circuit, a CMOS camera, a sensory processing circuit, a transducer, a piezoelectric transducer, an ultrasound producing element, an ultrasound receiving element, a diode, a passive electrical element, a bypass capacitor, an optical element, a lens, a waveguide, a grating, a diffraction grating, a Bragg grating, a chemiluminescent film, a chemiluminescent microfluidic structure, etc. The components may be conductively coupled to the one or more conducting members of the elongated conductor using any of a variety of different approaches. The protocol employed may be chosen based on the particular pattern of insulation openings to which the component is to be coupled.

In some instances, the components to be connected include multiple individual connections which are configured to correspond to the pattern of insulation openings of the elongated conductor, thereby provided for rapid, single step operative coupling, where desired. For example, where the elongated conductor region, e.g., proximal region, includes an axially aligned pattern of insulation openings, the following protocol may be employed to readily couple a connector having multiple individual connection elements. The proximal pattern of the aligned conductors, e.g., wires, may be staggered axially along the length of the assembly such that once wound, each wire is only exposed along a length of the assembly at a known, predetermined location relative to the elongated conductor as a whole. Then, the distance from the proximal end is a parameter that can be used to automatically encode each wire in the assembly, e.g., such that the pattern of insulation openings at the proximal end is axially encoded. In this way, the conductor may be viewed as one whose proximal region is an axially encoded connector region. With respect to the connector in such a protocol, an array of multiple individual connection elements may be prefabricated from a sheet of parent structure. During fabrication, the array of individual connection elements may be formed around the proximal end of the assembly, preformed, etc. Examples of such encoding are evident throughout this disclosure and are particularly highlighted in FIGS. 4A-4B.

In some instances, the connector array may be associated with the elongated conductor at the proximal region, and a single attachment process used to operatively couple each individual connection element of the connector to the associated wire in the assembly (as determined by axial positioning and encoding of the connectors and assembly wires), e.g., by simultaneous press-fitting each connection element about its insulation opening. Any additional molding, intermediate material placement, etc. may be applied to the structure, as desired. The support structure of the connector array, if present, may be removed. Optionally, the entire structure may be swaged down to the final size, as desired.

In those instances where the elongated conductor region, e.g., distal region, includes a transversely aligned pattern of insulation openings, the following protocol may be employed to readily operatively couple a component, such as a flex assembly, to the elongated conductor. While aligned, the aligned conducting members, e.g., wires, are stably associated with a substrate. Either before or after substrate attachment, a pattern of insulation openings is produced in the conducting members, e.g., using a protocol as described above. The pattern of insulation openings may be a transverse pattern across the conducting members, where the distance from a flanking conducting member is a parameter that can be used to automatically encode each conducting member in the assembly. In this way, the elongated conductor may be viewed as one whose distal region is a transversely encoded connector region. The pattern may be one that allows for simplified reflow attachment to a flex substrate, attachment via a z-axis adhesive, a patterned conductive adhesive, etc. Spacing, patterns, etc. can be easily controlled so as to optimize the subsequent flex assembly attachment. Where desired a single "flip-chip" like assembly operation may be employed. Optionally, the pattern may be modified, e.g., by pre-wetting, plating-up, or "bumping" one or more of the openings, as desired, so as to more readily make connections to a flex assembly. Where desired, the conducting members near the connector may be collectively arranged so as to form a micro-strain relief. This approach further helps to maintain the mechanical robustness of the overall device after completed.

FIG. 8A provides a schematic of portions of a method of fabricating an elongated conductor, in accordance with an embodiment of the invention. FIG. 8A shows the steps of patterning one or more windows into the conducting members, arranging the conducting members together so as to form a desired pattern between the windows and a desired shape of the assembly, and forming one or more structures from the assembly, such as fixing relative positioning of the conducting members with a method in accordance with the present disclosure.

FIGS. 9A-9B provide illustrations of steps of a method for fabricating an elongated conductor 900, in accordance with an embodiment of the invention. FIG. 9A shows a method for patterning 903 an array of windows into the insulation 910 of the conducting members of the elongated conductor 900 wherein the conducting element 907 of the conducting member is exposed in the vicinity of each patterned window. The method illustrates some non-limiting patterns, including single circumferential stripped insulation 905, half circumferential stripped insulation 915, circle shaped stripped insulation 920, elongated regions of stripped insulation 925, an array of circular windows 930 on a single conducting member, and an array of circumferentially stripped insulation 935. The patterned windows 905, 915, 920, 925, 930, 935 collectively form a patterned region. After patterning, the conductive members are optionally arranged 940 into a final configuration 945. In this non-limiting example, the final configuration 945 is fixed by attachment to a supporting substrate 947 (e.g., a component, a simple supporting film, an interposer, an integrated circuit, a flexible circuit, etc.). In some instances, the patterns may be arranged such that the conducting members may be directly interfaced with a target component, or the like.

FIG. 9B provides an illustration of a method for patterning 953 an array of windows 955, 960, 965, 970, 975, 980 into the insulation of the conducting members of the elongated conductor 950 wherein the conducting elements of the conducting member are exposed in the vicinity of each patterned window 955, 960, 965, 970, 975, 980. In this non-limiting example, the patterned windows 955, 960, 965, 970, 975, 980 are arranged axially along the length of the conducting members, such that, at each position along the length of the elongated conductor 950, particular conducting members are windowed, and other conducting members are insulated. FIG. 9B also shows bringing the conducting members together 985 (i.e. in this non-limiting instance, wrapping them around a mandrel), and forming a final shape 990 (i.e. in this non-limiting instance a helical tubular structure). In some instances, additional elements may be added to the assembly to alter the properties thereof. Additional wires may be added to form a shield, structural fibers may be integrated so as to strengthen the final shape 990, etc.

Figure 10A:
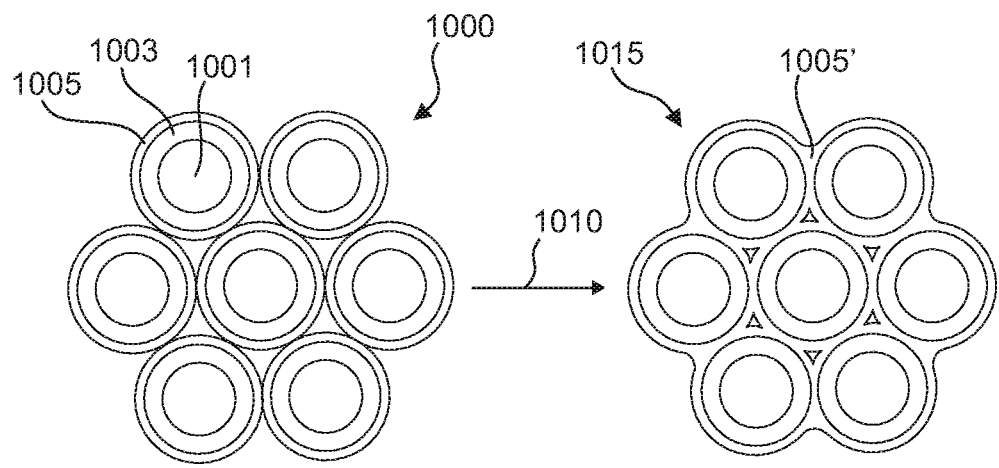
FIGS. 10A and 10B provide illustrations of cross sections of an elongate conductor before and after a fixing step of a method for fabricating an elongated conductor, in accordance with an embodiment of the invention.
Figure 10B:
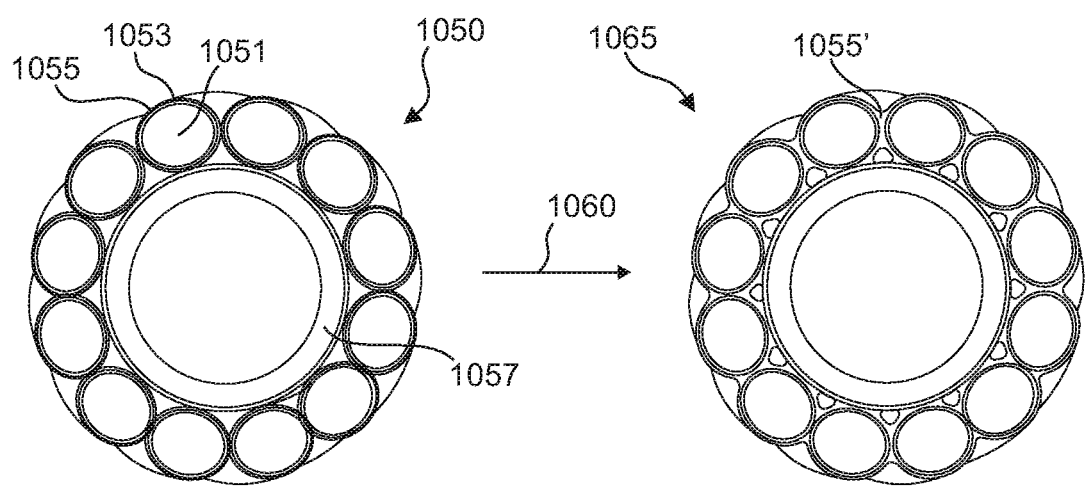

FIGS. 10A and 10B provide illustrations of cross sections of an elongate conductor before and after a fixing step of a method for fabricating an elongated conductor, in accordance with an embodiment of the invention. FIG. 10A shows a cross section of an elongated conductor 1000 with 7 conducting members 1001, each with a first insulation layer 1003, and a second binding layer 1005, the conducting members 1001 having been brought together during a previous operation. The assembly is then fixed 1010 to form a final assembly 1015 wherein the individual conducting members 1001 are structurally bound together through the modified second binding layer 1005'.

FIG. 10B shows a cross section of an elongated conductor 1050 including 12 conducting members 1051, each with a first insulating layer 1053, and a second binding layer 1055, the conducting members 1051 wrapped around a mandrel 1057 (i.e. in this case a thin walled tube configured to provide a lumen along the length of the elongated conductor 1050). The assembly is then fixed 1060 into a final assembly 1065 wherein the individual conducting members 1051 are at least somewhat held together with the modified second binding layer 1055'.

In some instances, the binding layer 1005, 1055 may be insulating. In other instances, the binding layer 1005, 1055 may be substantially conducting, so as to provide a shielding function for the conducting members 1001, 1051 in the elongated conductor 1000, 1050. In some instances, additional elements may be added to the assembly including, but not limited to: strengthening fibers, lumens (e.g., tubes), additional layers, additional insulating layers, split regions (i.e., forming the assembly into multiple pathways), addition of components, connectors, addition of optical fibers, etc.

Methods as described herein may be performed in a substantially, if not completely, continuous fashion, e.g., where each segment or split region is formed, wound, advanced and cut free (e.g., singulated), with the process being repeated as desired. The final assemblies may then be transferred to an alternative process, integrated into other devices, e.g., full catheters, guidewires, etc., as desired. In certain embodiments, the assemblies may be automatically built without having to color code or individually identify any of the conducting members, e.g., wires, in the assembly (e.g., where assembly formation and final build can be automated without the need for human intervention). In practicing embodiments of the invention, reliable assemblies may be produced by forming axially encoded connector contacts to transversely encoded contacts at either end of the assembly. In this manner, the end connections are reduced from wire-by wire (2×n identification and connection operations), to 2 operations (one placement and connection operation per end). The resultant elongated conductors of embodiments of the methods are mechanically robust, can be handled as a single unit (no need to handle the tiny wires individually), do not require color coding or individual conductor member identification, can be configured to readily include a bulk strain relief, and can be threaded through a very tight fitting super-assembly (e.g. a tube, shield, ring connector assembly, etc.), e.g., as described above.

Devices and Methods of Use

Elongated conductors of the invention, e.g., as described above, find use in a variety of different devices. In a general sense, the elongated conductors may be used to conductively, e.g., electrically, connect, any two components, where the components are conductively coupled to the conducting members of the elongated conductor at either end of the conductor. General types of devices in which the elongated conductors find use include, but are not limited to: communications devices, electronics devices, e.g., consumer and industrial electronics devices, transportation devices, medical devices, robotic assemblies, micro robotic devices, prosthetics, biosimilar devices, surgical devices, flexible conductor assemblies, automotive harnesses, etc.

With respect to medical devices, the elongated conductors find use in conductively, e.g., electrically, connecting, any two components, such as a proximal end connector and a distal end effector. Proximal end connectors may vary widely depending on the particular medical device in which the elongated conductor is employed, and are configured to serve as a connection between the elongated conductor (and effector coupled to the distal end thereof) and any of a variety of different devices, e.g., control devices, data processing devices, data display devices, power devices, communications devices, sensory devices, surgical implements, therapeutic devices, etc. A variety of different effectors may be conductively coupled to the distal end of the elongated conductor. Effectors that may be coupled to the distal end of the elongated conductors may be sensors and/or actuators. Sensing effectors of interest, i.e., sensors, may be configured to sense a variety of different types of data, such as but not limited to: electrical conductivity data, electrical potential data, pressure data, volume data, dimension data, temperature data, oxygen or carbon dioxide concentration data, hematocrit data, pH data, chemical data, blood flow rate data, thermal conductivity data, optical property data, cross-sectional area data, change in structure data, viscosity data, radiation data, monitoring an actuation process, and the like. Alternatively, the effectors may be configured for actuation or intervention, such as providing an electrical current or voltage, setting an electrical potential, heating a substance or area, inducing a pressure change, releasing or capturing a material, emitting light, emitting sonic or ultrasound energy, emitting radiation, orienting a tip, pushing against a surface, opening/closing a fluid channel, releasing a coil, and/or the like.

In some instances, the effector is electrically coupled to the elongated conductor via circuitry element, such as an integrated circuit. When present, integrated circuits may include a number of distinct functional blocks, i.e., modules, where the functional blocks are all present in a single integrated circuit on an intraluminal-sized support. By single integrated circuit is meant a single circuit structure that includes all of the different functional blocks. As such, the integrated circuit is a monolithic integrated circuit (also known as IC, microcircuit, microchip, silicon chip, computer chip or chip) that is a miniaturized electronic circuit (which may include semiconductor devices, as well as passive components) that has been manufactured in the surface of a thin substrate of semiconductor material. The integrated circuits of certain embodiments of the present invention are distinct from hybrid integrated circuits, which are miniaturized electronic circuits constructed of individual semiconductor devices, as well as passive components, bonded to a substrate or circuit board, such as may be supported on an interposer, an intermediate printed circuit board, an HDI flexible circuit, etc.

The support with which the circuit is associated, e.g., by being present on surface of the support or integrated, at least partially, inside of the support, may be any convenient support, and may be rigid or flexible as desired. Where the support is intraluminal sized, its dimensions are such that it can be positioned inside of a physiological lumen, e.g., inside of a vessel, such as a cardiac vessel, e.g., a vein or artery. In certain embodiments, the intraluminal sized integrated circuits have a size (e.g., in terms of surface area of largest surface) of between about 0.05 mm$^2$ and about 10 mm$^2$, such as between about 0.5 mm$^2$ and about 8 mm$^2$, and including about 1.5 mm$^2$. The supports of the integrated circuits can have a variety of different shapes, such as square, rectangle, oval, and hexagon, irregular, etc.

Devices, such as described above, may be produced using any convenient protocol. In some instances, methods of producing the devices include at least the following steps: providing an elongated conductor of the invention, e.g., as described above; and operatively, e.g., electrically, coupling a connector to the proximal end of the elongated conductor and an effector to the distal end of the elongated conductor, either directly or through an integrated circuit, e.g., as described above.

One type of medical device in which the elongated conductors find use is intraluminal medical devices, i.e., medical devices configured to be introduced into a lumen of a subject sense and/or modulate various physiological parameters, where examples of such devices include, but are not limited to catheter based devices, guidewire based devices, etc. An example of such a device is an interventional tool (e.g., a microsurgical tool) configured for monitoring electrophysiological activity within the vicinity of a lumen, the microsurgical tool including a one or more distinct sensing and/or actuating elements, e.g., in the form of microfingers, having a substantially elongate structure configured so as to bias a region thereof against a wall of the lumen upon deployment within the lumen, and a sensing tip electrically and mechanically coupled to the microfinger in the vicinity of the region, configured to interface with the wall of the lumen, the sensing tip configured to convey one or more electrophysiological signals associated with the activity. Such devices are further described in PCT application serial no. PCT/US2014/031962 published as WO2014160832 and titled "Neurological Traffic And Receptor Evaluation And Modification: Systems And Methods", the disclosure of which is herein incorporated by reference. Other such devices in which the elongated conductors find use include, but are not limited to: those devices described in: PCT application serial no. PCT/US2013/023157 published as WO 2013/112844 and titled "Controlled Sympathectomy and Micro-Ablation Systems and Methods"; PCT application serial no. PCT/US2013/042847 published as WO 2013/181137 and titled "Endoscopic Sympathectomy Systems and Methods"; PCT application serial no. PCT/US2013/045605 published as WO 2013/188640 and titled "Devices, Systems, And Methods for Diagnosis and Treatment of Overactive Bladder"; PCT application serial no. PCT/US2013/067726 published as WO 2014/070999 and titled: "Systems, Methods, And Devices For Monitoring And Treatment Of Tissues Within And/Or Through A Lumen Wall"; and PCT application serial no. PCT/US2013/073844 published as WO/2014/089553 and titled: "Systems and Methods for Regulating Organ and/or Tumor Growth Rates, Function, and/or Development"; the disclosures of which applications are herein incorporated by reference.

As disclosed in the above applications, use of such devices may include contacting the effector, e.g., sensor and/or actuator, of such a device to a tissue location of a living subject. Contact of the effector with tissue may be achieved via a variety of different protocols depending on the location of the target tissue, e.g., where the target tissue is internal, contact may be achieved via an intravascular approach. The devices may be employed with a variety of different types of subjects. Generally such subjects are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In certain embodiments, the subjects are humans. The methods may be diagnostic and/or therapeutic methods.

Aspects of the invention further include kits that include devices having an elongated conductor of the invention, e.g., as described above. Such kits at least include an elongated conductor, e.g., as described above. The kits may include one or more additional components that may find use with the device that includes the elongated conductor. The device (and other components when present) of the kits may be present in a suitable container, such as a sterile container, e.g., a sterile pouch.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another form of these instructions is a computer readable medium, e.g., portable flash drive, diskette, compact disk (CD), Hard Drive etc., on which the information has been recorded. Yet another form of these instructions that may be present is a website address which may be used via the internet to access the information at a removed site.

The following examples are offered by way of illustration and not be way of limitation.

EXPERIMENTAL

Example 1: Production of Elongated Conductor with 12 Conducting Members

An elongated conductor with 12 conducting members is formed. The conducting members are formed from a copper alloy (with nominal diameter of approximately 25 μm) with a first polyimide insulation layer (with thickness of approximately 3.5 μm) and a second polyvinyl butyral binding layer (with thickness of approximately 3 μm). The conducting members are arranged along a horizontal plane with approximately 0.5 mm spacing between individual conducting members, and the proximal and distal encoded windows are formed in the polyimide and polyvinyl butyral layers with an ultraviolet laser ablation source. In this non-limiting instance, the distal encoded windows are patterned so as to form a 2D array of windows (for later attachment to a planar component as a single connector) with windows substantially oriented to one side of the working plane, and the proximal encoded windows are patterned so as to form a substantially 1D axial array of windows (for later attachment to concentric connector elements), the windows being substantially fully circumferential windows around each wire at a spacing of 1.5 mm between window centers and a window sizing of 0.75 mm each along the wire lengths. The conducting members are then brought closer together through a fixture. The conducting members at the distal tip are arranged with a pitch of 45 μm (total width of 530 μm), and fixed through attachment to a reinforced thin tape element.

While the distal end is clamped just ahead of the fixed region, in a thermally protected arrangement, the remainder of the elongated conductor is wound about an axis, so as to form a tight cylindrical structure with a diameter of approximately 155 µm. The assembly is fixed into a final shape by application of heat from a heat gun, thus forming a final solidly connected assembly. The assembly is singulated to form a final assembly unit. The assembly unit is threaded through an extra-thin walled hypotube with an OD of 254 µm and a nominal ID of 190 µm. The resulting structure is ready for attachment of components to the ends thereof.

In this non-limiting example, the distal end is attached to a miniature HDI flexible circuit with pre-wetted contacts patterned so as to align with the distal end windows in the elongated conductor. The contacts are lined up, slight pressure is applied to the resulting interface and the pre-wetted contacts are reflowed to from a secure interconnection between the flexible circuit and the elongated conductor. Alternatively, in some instances, the attachment process may have been performed with a micro-patterned conductive adhesive, a z-axis adhesive, or the like.

In this non-limiting example, the proximal end is threaded through a concentric axial connector formed from a beryllium copper alloy with OD of 260 µm and an ID of 185 µm with pre-wetted inner surfaces on the contact pads of the connector. The whole connector is thermally reflowed when in position to form an interconnection between the elongated conductor and the connector. Support materials are cut away and the final connector is swaged to form a final cylindrical shape.

Such an arrangement may be advantageous for use as a micro guide wire in an interventional application.

Example 2: Production of Elongated Conductor with Distal Split Configuration

The same procedure is followed up until the step of attaching the distal region to the support. Instead the distal region is broken into two groups of 6 conducting members, and each of the groups is attached to a separate support so as to form a split arrangement. The total width of each split arrangement is 238 µm (40 µm pitch between conducting members). An additional 4 mm long length of the split regions is clamped before proceeding with the winding step outlined in Example 1. The split distal patterns are then attached to each side of an HDI flex circuit, so as to form a robust interconnect with a narrow overall width of 245 um. An ultra-thin walled polymer sheath is placed around the distal region to bridge across the hypotube to form a low profile distal part of the assembly. The distal region is potted with a silicone adhesive to form a secure structure at the distal end of the assembly.

Example 3: Elongated Conductor with Flexible Shield

An elongated conductor with 12 conducting members and a flexible shield is formed. The conducting members are formed from a copper alloy (with nominal diameter of approximately 25 µm) with a first polyimide insulation layer (with thickness of approximately 3.5 µm) and a second polyvinyl butyral binding layer (with thickness of approximately 3 µm). The conducting members are arranged along a horizontal plane with approximately 0.5 mm spacing between individual conducting members, and the proximal and distal encoded windows are formed in the polyimide and polyvinyl butyral layers with an ultraviolet laser ablation source. In this non-limiting instance, the distal encoded windows are patterned so as to form a 2D array of windows (for later attachment to a planar component as a single connector) with windows substantially oriented to one side of the working plane, and the proximal encoded windows are patterned so as to form a substantially 1D axial array of windows (for later attachment to concentric connector elements), the windows being substantially fully circumferential windows around each wire at a spacing of 1.5 mm between window centers and a window sizing of 0.75 mm each along the wire lengths. The conducting members are then brought closer together through a fixture. The conducting members at the distal tip are arranged with a pitch of 45 µm (total width of 530 µm), and fixed through attachment to a reinforced thin tape element. While the distal end is clamped just ahead of the fixed region, in a thermally protected arrangement, the remainder of the elongated conductor is wound about an axis, so as to form a tight cylindrical structure with a diameter of approximately 155 µm. The assembly is fixed into a final shape by application of heat from a heat gun, thus forming a final solidly connected assembly.

The flexible shield is formed from an array of less than 20 conducting members formed from a stainless steel wire with a nominal diameter of approximately 12.5 um and a polyamide insulation with thickness of approximately 7.5 um. In this non-limiting instance, the flexible shield is formed from 15 conducting members, which are wound about the wire assembly to form a final structure. Prior to winding, laser ablation is used to form windows in the insulation of the flexible shield conducting members such that an electrical interconnect may be formed there between after forming of the final structure. Once formed into position, the final structure is heated and cooled to form a final composite structure. The flexible shield is restrained with a thin electrically conducting band at either end to keep the wire elements in position and to make an electrical interconnect with the conducting members of the flexible shield during use.

The assembly is singulated to form a final assembly unit. The assembly unit is threaded through an extra-thin walled hypotube with an OD of 254 µm and a nominal ID of 190 µm. The resulting structure is ready for attachment of components to the ends thereof.

Example 4: Elongated Conductor with Controlled Impedance

An elongated conductor with 12 conducting members and two differential pairs each with a controlled impedance is formed. The conducting members are formed from a copper alloy (with nominal diameter of approximately 25 µm) with a first polyimide insulation layer (with thickness of approximately 3.5 µm) and a second polyvinyl butyral binding layer (with thickness of approximately 3 µm). The conducting members are arranged along a horizontal plane with approximately 0.5 mm spacing between individual conducting members, and the proximal and distal encoded windows are formed in the polyimide and polyvinyl butyral layers with an ultraviolet laser ablation source. In this non-limiting instance, the distal encoded windows are patterned so as to form a 2D array of windows (for later attachment to a planar component as a single connector) with windows substantially oriented to one side of the working plane, and the proximal encoded windows are patterned so as to form a substantially 1D axial array of windows (for later attachment to concentric connector elements), the windows being substantially fully circumferential windows around each wire at a spacing of 1.5 mm between window centers and a window sizing of 0.75 mm each along the wire lengths.

Two pairs of wires are brought separately together to form separate transmission line elements. Each pair is wound to form a separate pair, the pairs heated to fixate the associated conductive members so as to form two transmission lines. The conductor spacing between members of a pair is substantially determined by the wire diameter and the thickness of the first insulating layer. In this, non-limiting instance, the spacing between wires in the transmission line elements are approximately 32 µm apart and the high frequency characteristic impedance is approximately 75Ω.

The conducting members are then brought closer together through a fixture. The conducting members at the distal tip are arranged with a pitch of 45 µm (total width of 530 µm), and fixed through attachment to a reinforced thin tape element. While the distal end is clamped just ahead of the fixed region, in a thermally protected arrangement, the remainder of the elongated conductor is wound about an axis, so as to form a tight cylindrical structure with a diameter of approximately 155 µm. The assembly is fixed into a final shape by application of heat from a heat gun, thus forming a final solidly connected assembly. The differential lines are embedded in the assembly along with the other conducting members of the elongated conductor.

Example 5: Elongated Conductor with Flex Sensitive Region

An elongated conductor with 6 conducting members and 6 flex sensitive regions is formed. The conducting members are formed from a copper alloy (with nominal diameter of approximately 25 µm) with a first polyimide insulation layer (with thickness of approximately 3.5 µm) and a second polyvinyl butyral binding layer (with thickness of approximately 3 µm). The conducting members are arranged along a horizontal plane with approximately 0.05 mm spacing between individual conducting members, and the proximal and distal encoded windows are formed in the polyimide and polyvinyl butyral layers with an ultraviolet laser ablation source. In this non-limiting instance, the distal encoded windows are patterned so as to form a 2D array of windows (for later attachment to a planar component as a single connector) with windows substantially oriented to one side of the working plane, and the proximal encoded windows are patterned so as to form a substantially 1D axial array of windows (for later attachment to concentric connector elements), the windows being substantially fully circumferential windows around each wire at a spacing of 1.5 mm between window centers and a window sizing of 0.75 mm each along the wire lengths.

The distal 2D array of windows is provided so as to connect one or more sensors to the distal tip of the assembly, the axial array of windows is provided so as to connect one or more connector contacts to corresponding conducting members of the assembly.

Along the length of the wires, in the vicinity of the distal end, a series of insulation windows are formed in between alternating pairs of the conducting members. Windows with 0.5 mm length are formed at positions 1.0, 4.0, 6.0, 8.0, 10.0, and 12.0 mm from the distal end of the assembly (between wires 1-2, 2-3, 3-4, 4-5, 5-6, and 6-1). An ink made up of a mixture of a piezoresistive ink including a carbonyl nickel particle system and a silicone elastomer is provided with a filler to silicone ratio of 6:1 in a solvent carrier. A microvolume of ink is administered to the wire pairs at each of the windows so as to produce a bridge between the conducting members.

While the distal end is clamped just ahead of the fixed region, in a thermally protected arrangement, the remainder of the elongated conductor is wound about an axis, so as to form a tight cylindrical structure with a diameter of approximately 95 µm. The assembly is fixed into a final shape by application of heat from a heat gun, thus forming a final solidly connected assembly. The piezoresistive ink is cured during this thermal forming process.

Impedance between the conductive members of the finally formed elongated conductor will change as the conductive member is flexed in the vicinity of each of the windows. The impedance change can be tailored such that the high frequency impedance between adjacent wires may be measured to determine tip flexure of the elongated conductor, but low frequency signals may be communicated along the wires to a distal chip, integrated circuit, electrodes, or the like.

Embodiments of the invention provide a number of advantages that have been heretofore difficult or costly to achieve. With respect to the elongated conductors themselves, advantages include the ability to have insulation openings arranges in up to a 360 arrangement about the surface of the elongated conductor in the region of interest, e.g., the proximal and or distal region. Because of the methods employed to make the conductors, such can be readily achieved without unwanted destruction of insulation in adjacent conducting members. Elongated conductors of extremely small outer dimension are readily producible. In the elongated conductors, near ideal circular packing density (very high packing density) may be obtained, such that for a given wire count and core conductor size, an assembly of much smaller diameter than has been heretofore possible may be produced. Similarly, for a given overall diameter, much larger core conductor diameters can packed into the conductor, which provides for desirable impedance, strength, and other properties. Controlled impedance is also achievable, in that the insulation properties and thicknesses can be precisely controlled, which upon bringing the various conducting members together in the assembly, provides for precise control of the impedance between adjacent wires along the length of the assembly. For a given wire diameter, a much finer pitch than heretofore possible may be obtained. Truly concentric axial encoding is obtainable in the elongated conductors of the invention.

Notwithstanding the appended clauses, the disclosure is also defined by the following clauses:
1. An elongated conductor comprising:
    an elongated structure having a proximal region and a distal region and comprising two or more insulated conducting members that are in fixed relative position along at least a portion of the elongated structure and extend from the proximal region to the distal region; and a pattern of insulation openings among the insulated conducting members at one or both of the proximal and distal regions.
2. The elongated conductor according to Clause 1, wherein the elongated structure comprises a first pattern of insulation openings among the insulated conducting members at the proximal region and a second pattern of insulation openings among the insulated conducting members at the distal region.
3. The elongated conductor according to Clauses 1 or 2, wherein the elongated conductor comprises a transversely aligned pattern of insulation openings.

4. The elongated conductor according to Clauses 1 or 2, wherein the elongated conductor comprises an axially aligned pattern of insulation openings.
5. The elongated conductor according to any of Clauses 1 to 4, wherein the elongated conductor comprises both a transversely aligned pattern of insulation openings and an axially aligned pattern of insulation openings.
6. The elongated conductor according to any of the preceding clauses, wherein the structure comprises from 2 to 500 insulated conducting members.
7. The elongated conductor according to any of the preceding clauses, wherein at least a portion of the elongated conductor is cylindrical.
8. The elongated conductor according to any of the preceding clauses, wherein the insulated conducting members assume a wound configuration along at least a portion of the elongated structure.
9. The elongated conductor according to any of the preceding clauses, wherein the insulated conducting members assume a braided configuration along at least a portion of the elongated structure.
10. The elongated conductor according to any of the preceding clauses, wherein the elongated conductor controlled impedance.
11. The elongated conductor according to any of the preceding clauses, wherein the insulated conducting members are configured to define a lumen along at least a portion of the elongated structure.
12. The elongated conductor according to Clause 11, wherein the lumen has a diameter ranging from 0.025 to 20.0 mm.
13. The elongated conductor according to any of the preceding clauses, wherein elongated conductor comprises an insulated conducting member packing density ranging from 30 to 90%.
14. The elongated conductor according to any of the preceding clauses, wherein elongated conductor comprises an insulated conducting member pitch ranging from 6 to 250 µm.
15. The elongated conductor according to any of the preceding clauses, wherein the insulated conducting members are not in fixed relative position along at least a portion of the elongated structure.
16. The elongated conductor according to any of the preceding clauses, wherein the insulated conducting members are not present in a wound configuration along at least a portion of the elongated structure.
17. The elongated conductor according to any of the preceding clauses, wherein the two or more insulated conductors comprise conductors of differing diameter.
18. The elongated conductor according to any of the preceding clauses, wherein the elongated conductor comprises a central insulated conductor surrounded by a plurality of peripheral insulated conductors.
19. The elongated conductor according to any of the preceding clauses, wherein the insulated conducting members are present in a sheath.
20. The elongated conductor according to Clause 19, wherein the sheath comprises a conductive material.
21. The elongated conductor according to Clause 19, wherein the sheath comprises an insulating material.
22. The elongated conductor according to any of Clauses 19 to 21, wherein the sheath comprises a water impermeable material.
23. The elongated conductor according to any of the preceding clauses, wherein the elongated conductor comprises an electrical shield component.
24. The elongated conductor according to Clause 23, wherein the electrical shield component comprises a sheath.
25. The elongated conductor according to Clause 23, wherein the electrical shield component comprises one or more wires.
26. The elongated conductor according to Clause 23, wherein the electrical shield component comprises a conductive insulating layer of one or more electrical conductors.
27. The elongated conductor according to Clause 23, wherein the electrical shield component comprises a binding layer of the elongated conductor.
28. The elongated conductor according to any of the preceding clauses, wherein the insulated conducting members of at least one of the proximal and distal regions are stably associated with a substrate.
29. The elongated conductor according to any of the preceding clauses, wherein the insulated conductors comprise a conductive core present in an insulating coating.
30. The elongated conductor according to Clause 29, wherein the conductive core comprises an electrically conductive material.
31. The elongated conductor according to any of Clauses 29 to 30, wherein the insulating coating comprises a thermostable material.
32. The elongated conductor according to Clauses 29 to 31, wherein conductive members are stably associated with each other by a thermoplastic material.
33. The elongated conductor according to any of the preceding clauses, wherein the elongated conductor is dimensioned to be positioned in mammalian vasculature.
34. The elongated conductor according to any of the preceding clauses, wherein the elongated conductor has a length ranging from 5 to 4,000 mm.
35. The elongated conductor according to any of the preceding clauses, wherein the elongated conductor has an outer diameter ranging from 75 µm to 5 mm.
36. The elongated conductor according to any of the preceding clauses, wherein the insulated conductors of at least one of the proximal and distal regions assume a split configuration.
37. The elongated conductor according to Clause 36, wherein the split configuration is configured to provide for operative coupling to opposing sides of a component.
38. The elongated conductor according to Clause 36, wherein the split configuration is configured to provide for operative coupling to the same side of a component.
39. The elongated conductor according to any of the preceding clauses, wherein the elongated conductor is configured to be employed in a sensing device.
40. The elongated conductor according to any of the preceding clauses, wherein the elongated conductor is configured to be employed in an actuating device.
41. The elongated conductor according to any of the preceding clauses, wherein the elongated conductor is configured to be employed in sensing and actuating device.
42. The elongated conductor according to any of the preceding clauses, wherein the elongated conductor comprises a piezo component.
43. The elongated conductor according to Clause 42, wherein the piezo component comprises a piezoresistive component.
44. The elongated conductor according to Clause 42, wherein the piezo component comprises a piezoelectric component.

45. The elongated conductor according to any of the preceding clauses, wherein the elongated conductor is configured to function as a guidewire.
46. The elongated conductor according to any of the preceding clauses, wherein the elongated conductor comprises a radiopaque region.
47. The elongated conductor according to Clause 46, wherein the radiopaque region comprises a marker band.
48. A method of making an elongated conductor, the method comprising:
   aligning two or more insulated conducting members in an elongated configuration having a proximal region and a distal region; and
   producing a pattern of insulation openings among the insulated conducting members at one or both of the proximal and distal regions.
49. The method according to Clause 48, further comprising fixing the relative position of the two or more insulated conducting members along at least a portion of the elongated conductor.
50. The method according to Clause 49, wherein the relative position of the two or more insulated conducting members is fixed after the pattern of insulation openings is produced.
51. The method according to Clause 49, wherein the relative position of the two or more insulated conducting members is fixed before the pattern of insulation openings is produced.
52. The method according to any of Clauses 48 to 51, wherein the method comprises producing a first pattern of insulation openings among the insulated conducting members at the proximal region and a second pattern of insulation openings among the insulated conducting members at the distal region.
53. The method according to any of Clauses 48 to 52, wherein pattern of insulation openings is transversely aligned.
54. The method according to any of Clauses 48 to 52, wherein the pattern of insulation openings is axially aligned.
55. The method according to any of Clauses 48 to 54, wherein the method comprises producing both a transversely aligned pattern of insulation openings and an axially aligned pattern of insulation openings.
56. The method according to any of Clause 48 to 56, wherein the method comprises winding the insulated conducting members.
57. The method according to Clause 56, wherein the insulated conducting members are wound about a mandrel.
58. The method according to Clause 57, wherein the method comprises separating the mandrel from the wound insulated conducting members to produce a lumen in the elongated structure.
59. The method according to any of Clauses 48 to 58, wherein the method comprises inserting the aligned insulating conductors into a first sheath.
60. The method according to Clause 59, wherein the method further comprises inserting a second sheath into the first sheath between the first sheath and the insulated conducting members.
61. The method according to Clause 60, wherein the method comprises separating the first sheath from the second sheath and insulating conducting members.
62. The method according to any of Clauses 59 to 61, wherein at least one of the sheaths comprises a conductive material.
63. The method according to any of Clauses 59 to 62, wherein at least one of the sheaths comprises an insulating material.
64. The method according to any of Clauses 48 to 63, wherein the method comprises stably associating at least one of the proximal and distal regions with a substrate.
65. The method according to any of Clauses 48 to 64, wherein the insulated conductors comprise a conductive core present in an inner insulating coating and an outer coating.
66. The method according to Clause 65, wherein the conductive core comprises an electrically conductive material.
67. The method according to Clauses 65 or 66, wherein the outer coating comprises a thermoplastic material.
68. The method according to any of Clauses 65 to 67, wherein the inner insulating coating comprises a thermally stable material.
69. The method according to any of Clauses 67 to 68, wherein the method comprises heating the thermoplastic material in a manner sufficient to fix the relative position of the insulted conductors.
70. The method according to any of Clauses 48 to 69, wherein the elongated conductor is dimensioned to be positioned in mammalian vasculature.
71. The method according to any of Clauses 48 to 70, wherein the elongated conductor has a length ranging from 5 to 4,000 mm.
72. The method according to any of Clauses 48 to 71, wherein the elongated conductor has an outer diameter ranging from 75 μm to 5 mm.
73. The method according to any of Clauses 48 to 72, wherein the method is a continuous process.
74. A device comprising:
   an elongated conductor according to any of Clauses 1 to 47; a connector positioned at the proximal end of the elongated conductor; and an effector positioned at the distal end of the elongated conductor.
75. The device according to Clause 74, wherein the effector comprises a sensor.
76. The device according to Clause 75, wherein the sensor is electrically coupled to the insulated conductors by an integrated circuit.
77. The device according to any of Clauses 75 to 76, wherein the sensor comprises a plurality of distinct sensing elements.
78. The device according to Clause 74, wherein the effector comprises an actuator.
79. A method of making a device, the method comprising:
   providing an elongated conductor according to any of Clauses 1 to 47; and
   operatively coupling a connector to the proximal end of the elongated conductor and an effector to the distal end of the elongated conductor.
80. The method according to Clause 79, wherein the effector comprises a sensor.
81. The method according to Clause 80, wherein the sensor is electrically coupled to the insulated conductors by an integrated circuit.
82. The method according to any of Clauses 80 to 81, wherein the sensor comprises a plurality of distinct sensing elements.
83. The method according to Clause 79, wherein the effector comprises an actuator.
84. The method according to any of Clauses 79 to 83, wherein the method comprises producing the elongated conductor.

85. The method according to Clause 84, wherein the elongated conductor is produced by a method according to any of Clauses 1 to 27 (see above, section II).
86. A method comprising contacting the effector of a device according to any of Clauses 74 to 78 with a tissue location of a living subject.
87. The method according to Clause 86, wherein the tissue location comprises, a cavity, a vessel or an organ location.
88. The method according to Clauses 86 to 87, wherein the living subject is a mammal.
89. The method according to Clause 88, wherein the mammal is a human.
90. The method according to any of Clauses 86 to 89, wherein the method is a diagnostic method.
91. The method according to any of Clauses 86 to 90, wherein the method is a therapeutic method.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A device comprising:
   (a) an elongated conductor comprising:
      (i) an elongated structure having a proximal region and a distal region and comprising two or more insulated conducting members that are in fixed relative position along at least a portion of the elongated structure and extend from the proximal region to the distal region; and
      (ii) a pattern of insulation openings among the insulated conducting members at one or both of the proximal and distal regions;
   (b) a connector positioned at the proximal end of the elongated conductor; and
   (c) an effector positioned at the distal end of the elongated conductor.
2. The device according to claim 1, wherein the effector comprises a sensor.
3. The device according to claim 2, wherein the sensor is electrically coupled to the insulated conductors by an integrated circuit.
4. The device according to claim 2, wherein the sensor comprises a plurality of distinct sensing elements.
5. The device according to claim 1, wherein the effector comprises an actuator.
6. The device according to claim 1, wherein the elongated structure comprises a first pattern of insulation openings among the insulated conducting members at the proximal region and a second pattern of insulation openings among the insulated conducting members at the distal region.
7. The device according to claim 1, wherein the elongated conductor comprises a transversely aligned pattern of insulation openings.
8. The device according to claim 1, wherein the elongated conductor comprises an axially aligned pattern of insulation openings.
9. The device according to claim 1, wherein the elongated conductor comprises both a transversely aligned pattern of insulation openings and an axially aligned pattern of insulation openings.
10. The device according to claim 1, wherein at least a portion of the elongated conductor is cylindrical.
11. The device according to claim 1, wherein the elongated conductor controlled impedance.
12. The device according to claim 1, wherein the insulated conducting members are configured to define a lumen along at least a portion of the elongated structure.
13. The device according to claim 1, wherein the elongated conductor is dimensioned to be positioned in mammalian vasculature.
14. A method of making a device, the method comprising:
   providing an elongated conductor comprising:
      an elongated structure having a proximal region and a distal region and comprising two or more insulated conducting members that are in fixed relative position along at least a portion of the elongated structure and extend from the proximal region to the distal region; and
      a pattern of insulation openings among the insulated conducting members at one or both of the proximal and distal regions; and
   operatively coupling a connector to the proximal end of the elongated conductor and an effector to the distal end of the elongated conductor.
15. The method according to claim 14, wherein the effector comprises a sensor.
16. The method according to claim 15, wherein the sensor is electrically coupled to the insulated conductors by an integrated circuit.
17. The method according to claim 15, wherein the sensor comprises a plurality of distinct sensing elements.
18. The method according to claim 14, wherein the effector comprises an actuator.
19. The method according to claim 14, wherein the method comprises producing the elongated conductor.
20. The method according to claim 19, wherein the elongated conductor is produced by a method comprising:
   aligning two or more insulated conducting members in an elongated configuration having a proximal region and a distal region; and
   producing a pattern of insulation openings among the insulated conducting members at one or both of the proximal and distal regions.

* * * * *